United States Patent [19]

Mutsukado et al.

[11] Patent Number: 5,098,900
[45] Date of Patent: * Mar. 24, 1992

[54] 3(2H)PYRIDAZINONE, PROCESS FOR ITS PREPARATION AND ANTI-ALLERGIC AGENT CONTAINING IT

[75] Inventors: Motoo Mutsukado, Sakura; Keizo Tanikawa, Tokyo; Ken-ichi Shikada, Kuki; Ryozo Sakoda, Kashiwa, all of Japan

[73] Assignee: Nissan Chemical Industries Ltd., Tokyo, Japan

[*] Notice: The portion of the term of this patent subsequent to Jan. 9, 2007 has been disclaimed.

[21] Appl. No.: 180,599

[22] Filed: Apr. 11, 1988

Related U.S. Application Data

[63] Continuation of Ser. No. 806,812, Dec. 10, 1985, abandoned.

Foreign Application Priority Data

Dec. 10, 1984 [JP] Japan ................ 59-260342

[51] Int. Cl.⁵ ................ C07D 237/22; C07D 403/12; C07D 413/12; A61K 31/50
[52] U.S. Cl. ................ 514/212; 514/232.2; 514/236.2; 514/247; 514/826; 544/82; 544/114; 544/238; 544/239; 544/241; 540/598
[58] Field of Search ................ 544/82, 114, 238, 239, 544/241; 514/212, 232, 234, 247, 232.2, 236.2; 540/598

[56] References Cited

U.S. PATENT DOCUMENTS

| | | | |
|---|---|---|---|
| 4,360,672 | 11/1982 | Parg et al. ................ | 544/240 |
| 4,571,397 | 2/1986 | Taniguchi ................ | 544/238 |
| 4,892,947 | 1/1990 | Mutsukado ................ | 544/241 |
| 4,978,665 | 12/1990 | Tanikawa ................ | 544/239 |
| 5,011,839 | 4/1991 | Tanikawa ................ | 544/239 |

FOREIGN PATENT DOCUMENTS 784639 5/1968 Canada .

OTHER PUBLICATIONS

Chemical Abstracts, vol. 78, 72,037, Mar. 19, 1973, Karklina et al.: Reactions of 1-phenyl-4-nitro-5-chloro-6-pyridazone.
Chemical Abstracts, vol. 97, 55,755, Aug. 16, 1982, Matsuo et al.: Synthesis and Biological Activity of . . . .
Chemical Abstracts, vol. 89, 24,341a, Jul. 17, 1978, Matsuo et al.: Pyridazinone Derivatives.

*Primary Examiner*—Mark L. Berch
*Attorney, Agent, or Firm*—Oblon, Spivak, McClelland, Maier & Neustadt

[57] ABSTRACT

A 3(2H)pyridazinone of the formula:

wherein $R_1$ is $C_2$-$C_5$ alkyl; $R_2$ is hydrogen, $C_1$-$C_3$ alkyl, chlorine or bromine; $R_3$ is hydrogen or $C_1$-$C_4$ alkyl; and each of $Y_1$, $Y_2$ and $Y_3$ which may be the same or different, is hydrogen, $C_1$-$C_8$ alkyl, $C_2$-$C_8$ alkenyl, halogen, —$(CH_2)_lA$ [wherein A is substituted amino of the formula —$N(R_4)(R_5)$ (wherein each of $R_4$ and $R_5$ which may be the same or different, is $C_1$-$C_4$ alkyl, or $R_4$ and $R_5$ together form $C_4$-$C_6$ alkylene), morpholino, 4-$R_6$-piperazin-1-yl (wherein $R_6$ is $C_1$-$C_3$ alkyl) or —$OR_7$ (wherein $R_7$ is hydrogen or $C_1$-$C_3$ alkyl), and l is an integer of 0 to 3], —$OR_8$ [wherein $R_8$ is hydrogen, $C_1$-$C_8$ alkyl, $C_3$-$C_5$ alkenyl, benzyl or —$(CH_2)_q$—$R_9$ [wherein $R_9$ is $CO_2R_3$ (wherein $R_3$ is as defined above), —$CONHR_3$ (wherein $R_3$ is as defined above) or —$CH_2OR_7$ (wherein $R_7$ is as defined above), and q is an integer of 1 to 5]], —$CO_2R_3$ (wherein $R_3$ is as defined above), —$CON(R_{10})$ ($R_{11}$) [wherein each of $R_{10}$ and $R_{11}$ which may be the same or different, is hydrogen, $C_1$-$C_4$ alkyl or $C_3$-$C_5$ alkenyl, or $R_{10}$ and $R_{11}$ together form $C_4$-$C_6$ alkylene, —$(CH_2)_2O(CH_2)_2$— or —$(CH_2)_2N(R_6)(CH_2)_2$— (wherein $R_6$ is as defined above)], —$CONH(CH_2)_mA$ (wherein A is as defined above, and m is an integer of 2 to 4), —$CH$=$CHCOR_{12}$ (wherein $R_{12}$ is hydroxy, $C_1$-$C_4$ alkoxy or —$N(R_{13})$ ($CH_2)_nCO_2R_3$ (wherein $R_{13}$ is hydrogen, $C_1$-$C_6$ alkyl or cycloalkyl, $R_3$ is as defined above, and n is an integer of 1 to 4)), —$SR_{14}$ (wherein $R_{14}$ is $C_1$-$C_4$ alkyl), —CN or $$-\underset{\underset{O}{\|}}{C}R_3$$

wherein $R_3$ is as defined above), or two of $Y_1$, $Y_2$ and $Y_3$ together form (wherein p is an integer of 1 or 2), and a pharmaceutically acceptable salt thereof.

11 Claims, No Drawings

3(2H)PYRIDAZINONE, PROCESS FOR ITS PREPARATION AND ANTI-ALLERGIC AGENT CONTAINING IT

This application is a continuation of application Ser. No. 06/806,812, filed on Dec. 10, 1985, now abandoned.

BACKGROUND OF THE INVENTION

1. Field of the Invention

The present invention relates to a 3(2H)pyridazinone which exhibits antagonism against slow reacting substance of anaphylaxis (SRS-A) which induces a contraction of bronchial smooth muscle, and thus is useful as an anti-allergic agent, a process for its preparation and a pharmaceutical composition containing it.

2. Discussion of the Background

SRS-A is believed to be a principal etiologic substance which induces immediate allergy such as bronchial asthma or allergic rhinitis. Therefore, a medicine which controls the pharmacological effect of SRS-A, i.e. a SRS-A antagonist, is expected to be a useful anti-allergic agent.

However, a very few medicinal substances show antagonism against SRS-A, and no instance of their practical application has been reported.

As an example of a compound which is somewhat similar to the compound of the present invention, Canadian Patent 784,639 (hereinafter referred t as reference (a)) disclose 2-$C_1$-$C_8$-alkyl-4-chloro or bromo-5-benzylamino-3(2H)pyridazinone derivatives. However, the usefulness of the compounds disclosed in this reference (a) is restricted to a herbicide, and no mention is made as to its medical use or pharmacological activities.

As another example of a compound similar to the compound of the present invention, Chemical Abstract, 62, 2773b, (Bull. Soc. Chim, France, 1964 (9) p 2124-32) (reference (b)) discloses 2-methyl-4-chloro or bromo-5-benzylamino-3(2H)pyridazinones. This reference (b) is silent about medical use or pharmacological activities.

Likewise, as still another example of a compound similar to the compound of the present invention, published German Patent Application No. 1670169 (published on Nov. 5, 1970) (reference (c)) discloses 2-alkyl-4-chloro-5-arylalkylamino-3(2H)pyridazinones. This reference (c) discloses a process for the synthesis of pyridazinones including such compounds, their application for agricultural chemicals, their application as intermediates for medicines or dyestuffs, or their application as intermediates for various compounds. However, no mention is made to their pharmacological activities, and no specific examples are given for such compounds. Further, such compounds are not specifically described.

SUMMARY OF THE INVENTION

The present inventors have synthesized and studied various compounds for antagonistic activities against SRS-A, and it has been surprisingly found that 3(2H)pyridazinones of the formula I and their pharmaceutically acceptable salts exhibit antagonistic activities against SRS-A and thus are useful as an active ingredient for an anti-allergic agent.

DETAILED DESCRIPTION OF THE PREFERRED EMBODIMENTS

Namely, the present invention provides a 3(2H)pyridazinone of the formula:

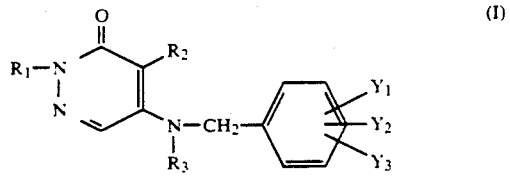

wherein $R_1$ is $C_2$-$C_5$ alkyl; $R_2$ is hydrogen, $C_1$-$C_3$ alkyl, chlorine or bromine; $R_3$ is hydrogen or $C_1$-$C_4$ alkyl; and each of $Y_1$, $Y_2$ and $Y_3$ which may be the same or different, is hydrogen, $C_1$-$C_8$ alkyl, $C_2$-$C_8$ alkenyl, halogen, —$(CH_2)_lA$ [wherein A is substituted amino of the formula —$N(R_4)(R_5)$ (wherein each of $R_4$ and $R_5$ which may be the same or different, is $C_1$-$C_4$ alkyl, or $R_4$ and $R_5$ together form $C_4$-$C_6$ alkylene), morpholino, 4-$R_6$-piperazin-1-yl (wherein $R_6$ is $C_1$-$C_3$ alkyl) or —$OR_7$ (wherein $R_7$ is hydrogen or $C_1$-$C_3$ alkyl), and l is an integer of 0 to 3], —$OR_8$ [wherein $R_8$ is hydrogen, $C_1$-$C_8$ alkyl, $C_3$-$C_5$ alkenyl, benzyl or —$(CH_2)_q$—$R_9$ [wherein $R_9$ is $CO_2R_3$ (wherein $R_3$ is as defined above), —$CONHR_3$ (wherein $R_3$ is as defined above) or —$CH_2OR_7$ (wherein $R_7$ is as defined above), and q is an integer of 1 to 5]], —$CO_2R_3$ (wherein $R_3$ is as defined above), —$CON(R_{10})(R_{11})$ [wherein each of $R_{10}$ and $R_{11}$ which may be the same or different, is hydrogen, $C_1$-$C_4$ alkyl or $C_3$-$C_5$ alkenyl, or $R_{10}$ and $R_{11}$ together form $C_4$-$C_6$ alkylene, —$(CH_2)_2O(CH_2)_2$— or —$(CH_2)_2N(R_6)(CH_2)_2$—(wherein $R_6$ is as defined above)], —$CONH(CH_2)_mA$ (wherein A is as defined above, and m is an integer of 2 to 4), —$CH=CHCOR_{12}$ (wherein $R_{12}$ is hydroxy, $C_1$-$C_4$ alkoxy or —$N(R_{13})(CH_2)_nCO_2R_3$ (wherein $R_{13}$ is hydrogen, $C_1$-$C_6$ alkyl or cycloalkyl, $R_3$ is as defined above, and n is an integer of 1 to 4)), —$SR_{14}$ (wherein $R_{14}$ is $C_1$-$C_4$ alkyl), —CN or

wherein $R_3$ is as defined above), or two of $Y_1$, $Y_2$ and $Y_3$ together form

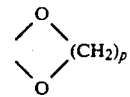

(wherein p is an interger of 1 or 2), and a pharmaceutically acceptable salt thereof.

Now, the present invention will be described with reference to the preferred embodiments.

Specific examples of substituents $R_1$, $R_2$, $R_3$, $Y_1$, $Y_2$ and $Y_3$ will be described. However, it should be understood that the present invention is by no means restricted to such specific examples.

$R_1$ is ethyl, n-propyl, i-propyl, n-butyl, sec-butyl, t-butyl, n-pentyl or i-pentyl;

$R_2$ is hydrogen, methyl, ethyl, n-propyl, i-propyl, chlorine or bromine;

$R_3$ is hydrogen, methyl, ethyl, n-propyl, i-propyl, n-butyl, i-butyl or sec-butyl; and Each of $Y_1$, $Y_2$ and $Y_3$ which may be the same or different, is hydrogen, methyl, ethyl, n-propyl, i-propyl, n-butyl, i-butyl, sec-butyl, n-pentyl, i-pentyl, n-hexyl, n-heptyl, n-octyl, vinyl, 1-propenyl, 1-butenyl, 1-pentenyl, 1-hexenyl, 1-heptenyl, 1-octenyl, fluorine, chlorine, bromine, iodine, dimethylamino, diethylamino, di-n-propylamino, di-n-butylamino, dimethylaminomethyl, diethylaminomethyl, di-n-propyl-aminomethyl, 2-dimethylaminoethyl, 2-diethylaminoethyl, 2-di-n-propylaminoethyl, dimethylaminopropyl, diethylaminopropyl, di-n-propylaminopropyl, morpholino, 4-methylpiperazin-1-yl, 4-ethylpiperazin-1-yl, 1-pyrrolidinyl, piperidino, hydroxy, methoxy, ethoxy, n-propoxy, hydroxymethyl, 2-hydroxyethyl, 3-hydroxypropyl, methoxymethyl, 2-methoxyethyl, ethoxymethyl, 2-ethoxyethyl, n-buthoxy, i-butoxy, sec-butoxy, n-pentyloxy, i-pentyloxy, n-hexyloxy, allyloxy, 3-butenyloxy, 2-butenyloxy, 4-pentenyloxy, 2-pentenyloxy, n-heptyloxy, n-octyloxy, benzyloxy, methylthio, ethylthio, n-propylthio, i-propylthio, n-butylthio, i-butylthio, sec-butylthio, carboxymethyloxy, methoxycarbonylmethyloxy, ethoxycarbonylmethyloxy, n-propoxycarbonylmethyloxy, 2-carboxyethyloxy, 2-methoxycarbonylethyloxy, 2-ethoxycarbonylethyloxy, 3-carboxypropyloxy, 3-methoxycarbonylpropyloxy, 3-ethoxycarbonylpropyloxy, 4-carboxybutyloxy, 4-methoxycarbonylbutyloxy, 4-ethoxycarbonylbutyloxy, 5-carboxypentyloxy, 5-methoxycarbonylpentyloxy, 5-ethoxycarbonylpentyloxy, carbamoylmethyloxy, methylaminocarbonylmethyloxy, ethylaminocarbonylmethyloxy, n-propylaminocarbonylmethyloxy, 2-(carbamoyl)ethyloxy, 2-(methylaminocarbonyl)ethyloxy, 2-(ethylaminocarbonyl)ethyloxy, 2-(n-propylaminocarbonyl)ethyloxy, 3-(carbamoyl)propyloxy, 3-(methylaminocarbonyl)propyloxy, 4-(carbamoyl)butyloxy, 4-(methylaminocarbonyl)butyloxy, 5-(carbamoyl)pentyloxy, 2-hydroxyethyloxy, 2-methoxyethyloxy, 2-ethoxyethyloxy, 2-propoxyethyloxy, 3-hydroxypropyloxy, 3-methoxypropyloxy, 3-ethoxypropyloxy, 4-hydroxybutyloxy, 4-methoxybutyloxy, 4-ethoxybutyloxy, 5-hydroxypentyloxy, 5-methoxypentyloxy, 5-ethoxypentyloxy, 6-hydroxyhexyloxy, 6-methoxyhexyloxy, 6-ethoxyhexyloxy, carboxyl, methoxycarbonyl, ethoxycarbonyl, n-propoxycarbonyl, i-propoxycarbonyl, n-butoxycarbonyl, i-butoxycarbonyl, carbamoyl, methylaminocarbonyl, ethylaminocarbonyl, allylaminocarbonyl, n-propylaminocarbonyl, n-butylaminocarbonyl, morpoholinocarbonyl, 4-methylpiperazin-1-yl-carbonyl, 4-ethylpiperazin-1-ylcarbonyl, piperidinocarbonyl, 2-dimethylaminoethylaminocarbonyl, 2-diethylaminoethylaminocarbonyl, 2-(di-n-propylamino)ethylaminocarbonyl, 2-piperidinoaminoethylcarbonyl, 3-dimethylaminopropylaminocarbonyl, 3-diethylaminopropylaminocarbonyl, 2-hydroxyethylaminocarbonyl, 2-methoxyethylaminocarbonyl, 2-ethoxyethylaminocarbonyl, 3-hydroxypropylaminocarbonyl, 3-methoxypropylaminocarbonyl, 3-ethoxypropylaminocarbonyl, 2-carboxyethenyl, 2-methoxycarbonylethenyl, 2-ethoxycarbonylethenyl, 2-(carboxymethylaminocarbonyl)ethenyl, 2-(methoxycarbonylmethylaminocarbonyl)ethenyl, 2-(ethoxycarbonylmethylaminocarbonyl)ethenyl, 2-(2-carboxyethylaminocarbonyl)ethenyl, 2-(2-methoxycarbonylethylaminocarbonyl)ethenyl, 2-(2-ethoxycarbonylethylaminocarbonyl)ethenyl, 2-(3-carboxypropylaminocarbonyl)ethenyl, 2-(3-methoxycarbonylpropylaminocarbonyl)ethenyl, cyano, formyl, acetyl or propionyl, or two of $Y_1$, $Y_2$ and $Y_3$ may together form —$OCH_2$— or —$OCH_2CH_2O$—.

Now, a process for the production of the compound of the formula I of the present invention will be described. The compound of the formula I may be prepared by the following reaction scheme 1:

Reaction scheme 1

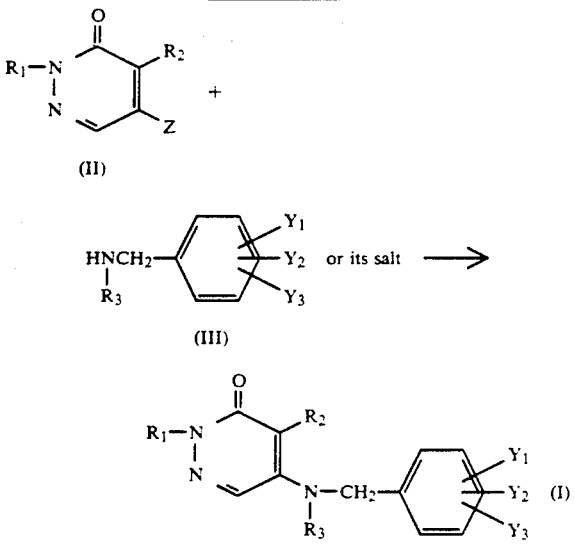

wherein $R_1$, $R_2$, $R_3$, $Y_1$, $Y_2$ and $Y_3$ are the same as defined above with respect to the formula I, and Z is chlorine or bromine.

Namely, the compound of the formula I can be prepared by reacting a 3(2H)pyridazinone compound of the formula II, i.e. one of starting materials, with a benzylamine derivative of the formula III or its acid salt in an inert solvent in the presence of a dehydrohalogenating agent as the case requires.

As the solvent, there may be employed an ether solvent such as diethyl ether, isopropyl ether, tetrahydrofuran or 1,4-dioxane, an amide solvent such as N,N-dimethylformamide, N,N-dimethylacetamide or N-methylpyrrolidone, dimethyl sulfoxide, an alcohol solvent such as methanol, ethanol or 1-propanol, a hydrocarbon solvent such as toluene or benzene, a ketone solvent such as acetone or methyl ethyl ketone, an organic amine solvent such as pyridine or a trialkylamine, or water.

In the above reaction, if $R_2$ is chlorine or bromine, there will be formed, in addition to the compound of the formula I, a compound of the formula:

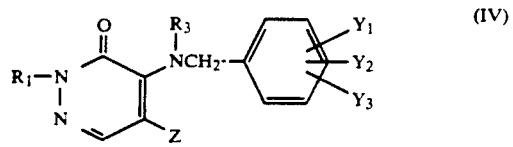

wherein $R_1$, $R_3$, Z, $Y_1$, $Y_2$ and $Y_3$ are the same as defined above with respect to the formula I, which is an isomer of the compound of the formula I with the 5-position substituted by benzylamino, as a by-product. The production rates of the compounds of the formulas I and IV depend upon the polarity of a solvent used. Namely, if a solvent having high polarity, such as water, a lower alcohol, an ether, an amide or dimethyl sulfoxide is used, the production rate of the compound of the formula I tends to be high. On the other hand, if a hydrocarbon solvent such as toluene or benzene is used, the production rate of the compound of the formula IV tends to increase.

Accordingly, in order to efficiently obtain the compound of the formula I, it is preferred to use a solvent having high polarity as mentioned above or to use a solvent mixture of water and an organic solvent, as the case requires.

The compound of the formula I may readily be separated and purified by fractional crystallization or by means of silica gel column chromatography.

As the dehydrohalogenating agent to be used, there may be employed an inorganic base, for instance, potassium carbonate, sodium carbonate or sodium hydrogencarbonate, and an organic base, for instance, a tertiary amine such as N,N-dimethylaniline, N,N-diethylaniline, trimethylamine or triethylamine, pyridine or methylethylpyridine. If necessary, a quarternary amine such as triethylbenzylammonium chloride may be added as an inter-phase transfer catalyst to the reaction system.

The reaction temperature may be within a range of from 10° C. to the boiling point of the solvent used for the reaction.

The molar ratios of the starting materials may optionally be set. However, it is common to use from 1 to 5 mols, preferably from 1 to 3 mols, of the benzylamine derivative of the formula III relative to 1 mol of the pyridazinone derivative of the formula II.

The 3(2H)pyridazinone compound of the formula II having a substituent at the 2-position, i.e. one of starting materials, wherein both $R_2$ and Z are the same and are chlorine or bromine, may be prepared by known processes as shown in reaction scheme 2 (for instance, Process 2-1 disclosed in Advances in Heterocyclic Chemistry, Vol. 9, p. 257(1968) or Process 2—2 disclosed in Chemical Abstract, 62, 2772g).

Reaction scheme 2

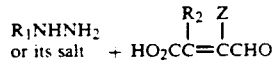

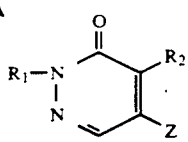

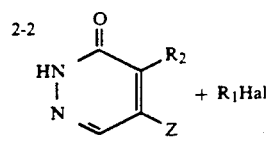

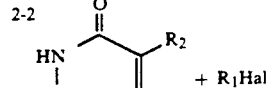

wherein $R_1$ is the same as defined above with respect to the formula I, and both $R_2$ and Z are chlorine or bromine.

Process 2-1 is a reaction for the production of the compound of the formula II by the ring closure reaction of a hydrazine or its acid salt with a mucochloric acid or mucobromic acid. Process 2—2 is a reaction for the production of the compound of the formula II by reacting 4,5-(dichloro or bromo)-3(2H)pyridazinone with a compound of the formula $R_1$-Hal (wherein $R_1$ is alkyl, and Hal is chlorine, bromine or iodine). For the production of the compound of the formula II, Process 2-1 or Process 2—2 may optionally be selected. While it is advantageous to employ Process 2-1 from the viewpoint of the yield and operation efficiency, it is usually advantageous to employ Process 2—2 when a hydrazine is commercially hardly available or difficult to produce economically.

The compound of the formula II wherein $R_2$ is $C_1$-$C_3$ alkyl, may be prepared by a process as shown in reaction scheme 3 or 4.

Reaction scheme 3

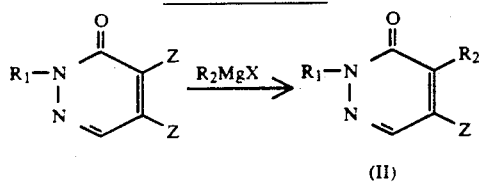

wherein $R_1$ and Z are the same as defined above with respect to the formula II; X is bromine or iodine, and $R_2$ is $C_1$-$C_3$ alkyl.

Namely, such a compound may readily be prepared by reacting a 2-alkyl-4,5-di-(chloro or bromo)-3(2H)-pyridazinone of the formula:

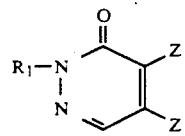

with a Grignard reagent of the formula $R_2MgX$ in the presence of an inert gas. As the solvent, there may be employed a hydrocarbon solvent such as toluene or benzene, and an ether solvent such as tetrahydrofuran or ethyl ether.

The reaction temperature may be within a range of from 0° C. to the boiling point of the solvent used for the reaction.

The molar ratios of the starting materials may optionally be set. However, it is common to use from 1 to 5 mols, preferably from 1 to 3 mols, of the Grignard reagent relative to 1 mol of the 4,5-di-(chloro or bromo)-3(2H)pyridazinone.

Reaction scheme 4

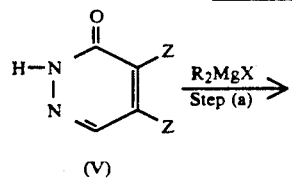

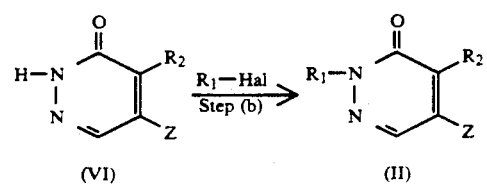

wherein $R_1$ and $R_2$ are the same as defined above with respect to reaction scheme 3, and Hal is the same as defined above with respect to Process 2—2.

Namely, the compound of the formula II may also be obtained by reacting 4,5-di-(chloro or bromo)-3(2H)-pyridazinone of the formula V having no substituent at the 2-position with a Grignard reagent of the formula $R_2MgX$ to obtain a compound of the formula VI, and reacting the compound of the formula VI with an alkyl halide of the formula $R_1Hal$.

Step (a) may be conducted under the conditions similar to those of the reaction scheme 3. Likewise, Step (b) may be conducted in the same manner as in reaction scheme 2—2.

With respect to the other starting material, i.e. a benzylamine of the formula:

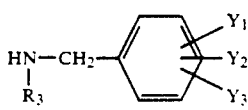

wherein $R_3$, $Y_1$, $Y_2$ and $Y_3$ are as defined above, the one which is hardly available as a commercial product, may be prepared by a known process for the preparation of a benzylamine as shown by reaction scheme 5.

Reaction scheme 5
Processes for the preparation of various benzylamines

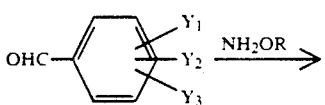

(wherein R is hydrogen or alkyl.)

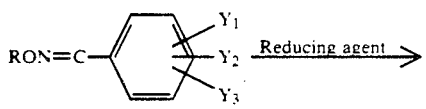

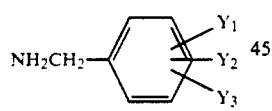

-continued
Reaction scheme 5
Processes for the preparation of various benzylamines

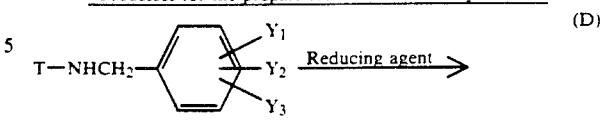

(wherein T is $C_2$-$C_4$ acyl or alkoxycarbonyl such as ethoxycarbonyl or t-butoxycarbonyl.)

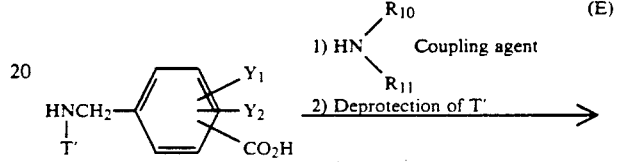

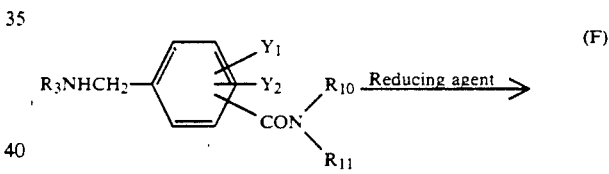

(wherein $R_{10}$ and $R_{11}$ are as defined above, and T' is alkoxycarbonyl such as ethoxycarbonyl or t-butoxy carbonyl.)

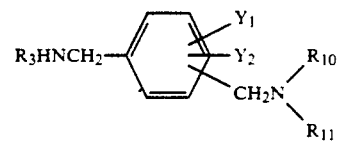

(wherein $R_{10}$ and $R_{11}$ are as defined above.)

In each of processes A, B and C, the desired benzylamine is prepared by the treatment of the starting material with a reducing agent. The starting material is an intermediate aldoxime prepared by reacting the corresponding aldehyde with hydroxyamine or alkoxyamine in the case of Process A, the corresponding nitrile in the case of Process B, or the corresponding amide in the case of Process C. In Process D, the desired N-alkyl substituted benzylamine is prepared by the treatment of the corresponding N-acyl substituted or N-alkoxycarbonyl substituted benzylamine with a reducing agent.

Any one of Processes A to D may optionally be employed by using a commercially available product or a starting material derived from such a commercial product. As a method for reduction, there is known (1) a method wherein Raney nickel (nickel-aluminum alloy) is used in the presence of an alkali metal hydroxide such as sodium hydroxide, or (2) a method wherein sodium borohydride is used in the presence of an acid such as -continued
TAAGAACATTTGATGCAAGATGGCCAGCACTGAACTT

TTGAGATATGACGGTGTACTTACTGCCTTGTAGCAAA

ATAAAGATGTGCCCTTATTTTAAAAAAAAAAAAAA

The initiation codon ATG appears at position 114, preceded by a 5'-untranslated region. The termination codon TGA at position 2034 is followed by a 3'-untranslated region spanning about 1200 nucleotides, which is followed by a poly(A) tail of about 140 nucleotides.

The antisense oligonucleotides of the invention may be synthesized by any of the known chemical oligonucleotide synthesis methods. Such methods are generally described, for example, in Winnacker, *From Genes to Clones: Introduction to Gene Technology.* VCH Verlagsgesellschaft mbH (H. Ibelgaufts trans. 1987).

Any of the known methods of oligonucleotide synthesis may be utilized in preparing the instant antisense oligonucleotides.

The antisense oligonucleotides are most advantageously prepared by utilizing any of the commercially available, automated nucleic acid synthesizers. The device utilized to prepare the oligonucleotides described herein, the Applied Biosystems 380B DNA Synthesizer, utilizes β-cyanoethyl phosphoramidite chemistry.

Since the complete nucleotide synthesis of DNA complementary to the c-myb mRNA transcript is known, antisense oligonucleotides hybridizable with any portion of the mRNA transcript may be prepared by the oligonucleotide synthesis methods known to those skilled in the art.

While any length oligonucleotide may be utilized in the practice of the invention, sequences shorter than 15 bases may be less specific in hybridizing to the target c-myb mRNA, and may be more easily destroyed by enzymatic digestion. Hence, oligonucleotides having 15 or more nucleotides are preferred. Sequences longer than 18 to 21 nucleotides may be somewhat less effective in inhibiting c-myb translation because of decreased uptake by the target cell. Thus, oligomers of 15-21 nucleotides are most preferred in the practice of the present invention, particularly oligomers of 15-18 nucleotides.

Oligonucleotides complementary to and hybridizable with any portion of the c-myb mRNA transcript are, in principle, effective for inhibiting translation of the transcript, and capable of inducing the effects herein described. It is believed that translation is most effectively inhibited by blocking the mRNA at a site at or near the initiation codon. Thus, oligonucleotides complementary to the 5'-terminal region of the c-myb mRNA transcript are preferred. It is believed that secondary or tertiary structure which might interfere with hybridization is minimal in this region. Moreover, it has been suggested that sequences that are too distant in the 3' direction from the initiation site may be less effective in hybridizing the mRNA transcripts because of a "read-through" phenomenon whereby the ribosome is postulated to unravel the antisense/sense duplex to permit translation of the message. See, e.g. Shakin, J. Biochemistry 261, 16018 (1986).

The antisense oligonucleotide is preferably directed to a site at or near the initiation codon for protein synthesis. Oligonucleotides complementary to a portion of the c-myb mRNA including the initiation codon (the first myb transcript, comprising nucleotides 114–116 of the complete transcript) are preferred, as are oligonucleotides complementary to the portion of the c-myb mRNA beginning with the codon adjacent to the initiation codon (the second codon from the 5' end of the translated portion, comprising nucleotides 117–119 of the complete transcript.

While antisense oligomers complementary to the 5'-terminal region of the c-myb transcript are preferred, particularly the region including the initiation codon, it should be appreciated that useful antisense oligomers are not limited to those complementary to the sequences found in the translated portion (nucleotides 114 to 2031) of the mRNA transcript, but also includes oligomers complementary to nucleotide sequences contained in, or extending into, the 5'- and 3'-untranslated regions. We have shown that oligomers whose complementarity extends into the 5'-untranslated region of the c-myb transcript are particularly effective in inhibiting translation. Oligomers having a nucleotide sequence complementary to a portion of the c-myb mRNA transcript including at least a portion of the 5'-untranslated region therefore comprise one group of preferred oligomers.

The following 15- through 21-mer oligodeoxynucleotides are complementary to the c-myb mRNA transcript beginning with the second codon of the translated portion of transcript (nucleotides 117–119 of the complete transcript):

5'-GCT GTG CCG GGG TCT TCG GGC-3'

5'-CT GTG CCG GGG TCT TCG GGC-3'

5'-T GTG CCG GGG TCT TCG GGC-3'

5'-GTG CCG GGG TCT TCG GGC-3'

5'-TG CCG GGG TCT TCG GGC-3'

5'-G CCG GGG TCT TCG GGC-3'

5'-CCG GGG TCT TCG GGC-3'

Similarly, the following 15- through 21-mer oligodeoxynucleotides are complementary to the c-myb mRNA transcript beginning with nucleotide 111 and extending through the initiation site:

5'-CCG GGG TCT TCG GGC CAT GGC-3'

5'-CG GGG TCT TCG GGC CAT GGC-3'

5'-G GGG TCT TCG GGC CAT GGC-3'

5'-GGG TCT TCG GGC CAT GGC-3'

5'-GG TCT TCG GGC CAT GGC-3'

5'-G TCT TCG GGC CAT GGC-3'

5'-TCT TCG GGC CAT GGC-3'

Oligonucleotides hybridizable to the c-myb mRNA transcript finding utility according to the present invention include not only native oligomers of the biologically significant nucleotides, i.e., A, dA, G, dG, C, dC, T and U, but also oligonucleotide species which have been modified for improved stability and/or lipid solubility. For example, it is known that enhanced lipid solubility and/or resistance to nuclease digestion results by substituting a methyl group or sulfur atom for a phosphate oxygen in the internucleotide phosphodiester Likewise, a compound of the formula X having —O—(CH$_2$)$_q$—R$_9$ (wherein R$_9$ and q are the same as defined above with respect to the formula I) may be prepared by reacting a compound of the formula VIII obtained by reaction scheme 8 with Hal—(CH$_2$)$_q$—R$_9$ of the formula IX (wherein Hal is the same as difined above with respect to reaction scheme 2—2 and R$_9$ is as defined above), as shown in reaction scheme 9.

(wherein Hal is as defined above, and R$_1$, R$_2$, R$_3$, R$_9$, Y$_1$, Y$_2$ and q are the same as defined above with respect to the formula I.) Alternatively, the object may also be attained by subjecting a compound of the formula XI, i.e. one of compounds obtained by the method of reaction scheme 9, to a usual organic reaction whereby the functional group R$_9$ is converted. One of specific examples will be shown in reaction scheme 10.

Reaction scheme 9

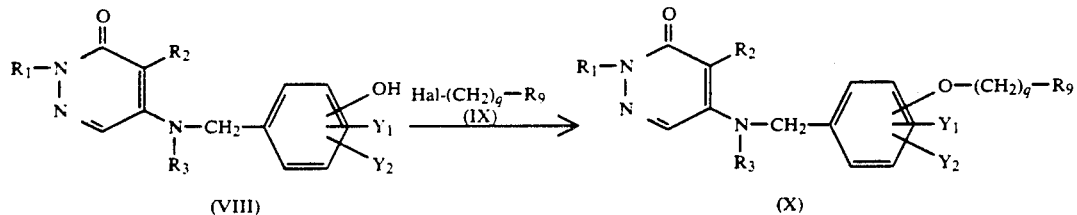

Reaction scheme 10

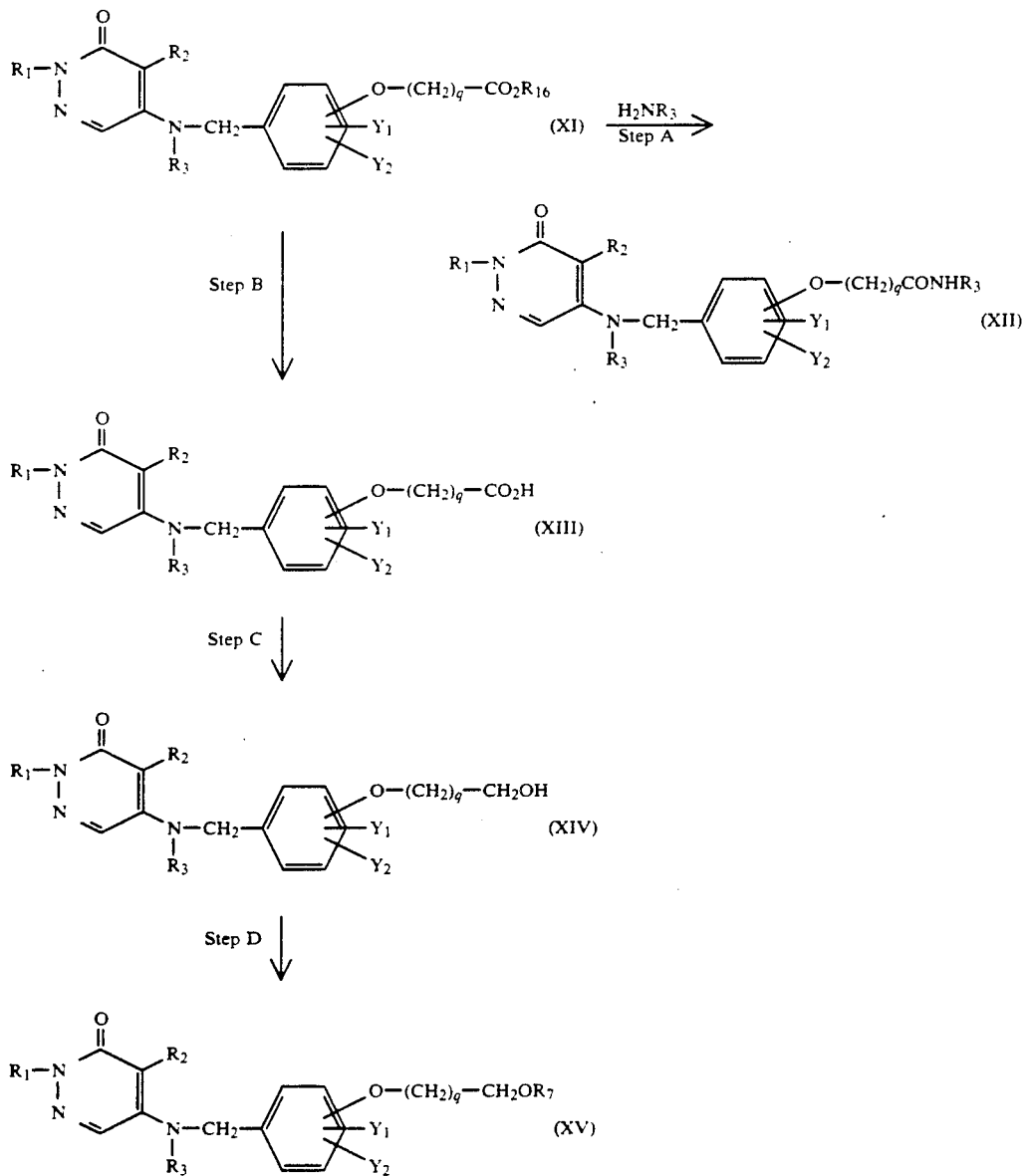

(wherein $R_1$, $R_2$, $R_3$, $R_7$, $Y_1$, $Y_2$, $Y_3$ and q are the same as defined above with respect to the formula I, and $R_{16}$ is $C_1$-$C_4$ alkyl.)

Step A is a process for preparing an amide of the formula XII by reacting —$CO_2R_{16}$ of the compound of the formula XI with $H_2NR_3$. Step B is a process for converting a compound of the formula XI to a carboxylic acid of the formula XIII by hydrolyzing it with a usual acid or alkali. Step C is a process for converting the carboxyl group of the compound of the formula XIII obtained in Step B to the alcohol of a compound of the formula XIV with a reducing agent such as sodium-bis-methoxyethoxyaluminum halide. Step D is a process for preparing a compound of the formula XV by alkylating the compound of the formula XIV obtained in Step C with e.g. an alkyl halide. (Specific manners for the respective steps will be given in Examples 5A-11A.)

The compound of the formula I wherein R is $C_1$-$C_3$ alkyl, may readily be prepared by reacting a compound of the formula XVI with a metal hydride and then reacting the product with an alkyl halide of the formula: $R_3$-Hal (wherein $R_3$ and Hal are as defined above), as shown in reaction scheme 11.

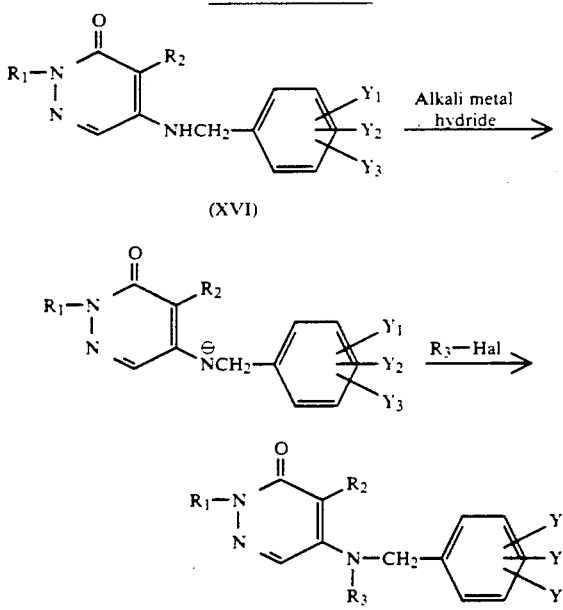

(wherein $R_1$, $R_2$, $R_3$, $Y_1$, $Y_2$ and $Y_3$ are the same as defined above with respect to the formula I, and Hal is as defined above.)

As the organic solvent to be used, it is preferred to use an inert organic solvent such as dimethylformamide or tetrahydrofuran. As the alkali metal hydride, sodium hydride is preferred. The reaction temperature is preferably within a range of from −40° to 10° C. in the case of the reaction with an alkali metal hydride, and within a range of from −15° to 70° C. in the case of the reaction with an alkyl halide.

The compound of the formula I wherein $R_2$ is hydrogen, may readily be prepared by dehalogenating the corresponding compound of the formula XVII wherein $R_2$ is chlorine or bromine by a hydrogen addition method (a common hydrogen addition method wherein palladium-carbon is used as a catalyst), as shown in reaction scheme 12.

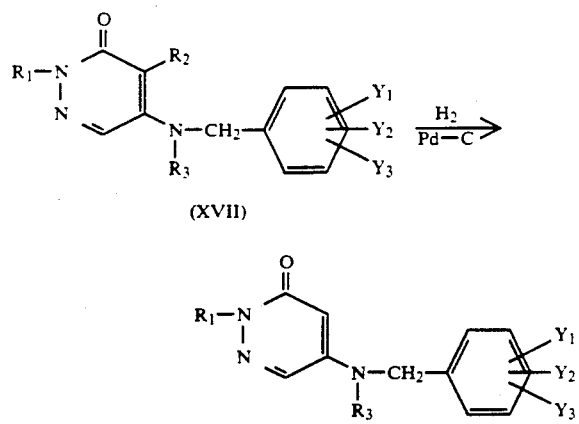

(wherein $R_1$, $R_3$, $Y_1$, $Y_2$ and $Y_3$ are the same as defined with respect to the formula, and $R_2$ is chlorine or bromine.)

As the organic solvent to be used, a usual inert solvent may be employed. However, it is particularly preferred to employ an alcohol solvent such as ethanol or methanol. An organic amine such as triethylamine or pyridine may be added whereby the reaction proceeds smoothly. The reaction temperature may be within a range of from 10° C. to the boiling point of the organic solvent used, but it is preferably within a range of from 20° to 60° C.

The compound of the formula I may readily be prepared by reacting 3(2H)pyridazinone of the formula XVIII having —$NHR_3$ (wherein $R_3$ is as defined above) at the 5-position with a benzyl halide of the formula XX or its derivative, as shown in reaction scheme 13. Namely, the compound of the formula I may also be prepared by reacting the 3(2H)pyridazinone of the formula XVIII with an alkali metal hydride such as sodium hydride in a solvent such as DMF or an ether solvent at a temperature of from 0 to 10° C. to form the corresponding anion compound of the formula XIX, and then reacting it with a benzyl halide of the formula XX.

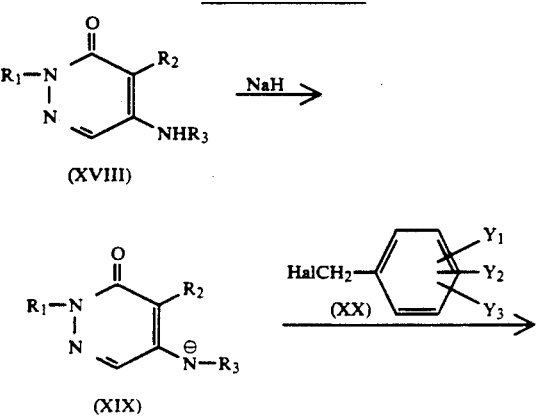

-continued
Reaction scheme 13

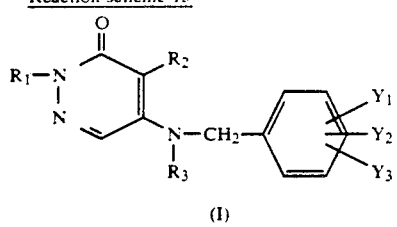

(I)

(wherein $R_1$, $R_2$, $R_3$, $Y_1$, $Y_2$, $Y_3$ and Hal are as defined above.)

The reaction may be conducted in the same conditions as those in reaction scheme 11.

Specific examples of the compounds covered by the present invention are, in addition to compounds described in Examples later in this specification, as follows:

4-chloro-5-(3-methoxycarbonyl-4-methoxybenzylamino)-2-t-butyl-3(2H)pyridazinone;
2,4-diethyl-5-(3,4-dimethoxybenzylamino)-3(2H)-pyridazinone;
4-chloro-5-(2-bromobenzylamino)-2-n-propyl-3(2H)-pyridazinone;
4-chloro-5-(3-n-pentyloxy-4-hydroxybenzylamino)-2-ethyl-3(2H)pyridazinone;
4-chloro-5-(3-n-pentyloxy-4-hydroxybenzylamino)-2-i-propyl-3(2H)pyridazinone;
4-chloro-5-(3-methoxy-4-hydroxybenzylamino)-2-ethyl-(2H)pyridazinone;
4-chloro-5-(3-methoxy-4-hydroxybenzylamino)-2-i-propyl-3(2H)pyridazinone;
4-chloro-5-(3-methoxy-4-hydroxybenzylamino)-2-n-propyl-3(2H)pyridazinone;
4-methyl-5-(2,4-dimethylbenzylamino)-2-ethyl-3(2H)pyridazinone;
4-methyl-5-(3-ethoxybenzylamino)-2-ethyl-3(2H)-pyridazinone;
4-methyl-5-(3-ethoxy-4-methoxybenzylamino)-2-ethyl-(2H)pyridazinone;
4-methyl-5-(3-n-propoxybenzylamino)-2-ethyl-3(2H)pyridazinone;
4-methyl-5-(3-n-propoxy-4-methoxybenzylamino)-2-ethyl-(2H)pyridazinone;
4-ethyl-5-(2,4-dimethylbenzylamino)-2-ethyl-3(2H)pyridazinone;
4-ethyl-5-(2,4-dimethoxybenzylamino)-2-ethyl-3(2H)pyridazinone;
4-ethyl-5-(3-ethoxybenzylamino)-2-ethyl-3(2H)-pyridazinone;
4-ethyl-5-(3-ethoxy-4-methoxybenzylamino)-2-ethyl-(2H)pyridazinone;
4-ethyl-5-(3-n-propoxybenzylamino)-2-ethyl-3(2H)pyridazinone;
4-ethyl-5-(3-n-propoxy-4-methoxybenzylamino)-2-ethyl-(2H)pyridazinone;
4-n-propyl-5-(2,4-dimethoxybenzylamino)-2-ethyl-3(2H)-pyridazinone;
4-methyl-5-(2,4-dimethylbenzylamino)-2-i-propyl-(2H)pyridazinone;
4-methyl-5-(2,4-dimethoxybenzylamino)-2-i-propyl-(2H)pyridazinone;
4-methyl-5-(3-ethoxy-4-methoxybenzylamino)-2-i-propyl-(2H)pyridazinone;
4-methyl-5-(3-n-propoxy-4-methoxybenzylamino)-2-i-propyl-3(2H)pyridazinone;
4-ethyl-5-(2,4-dimethoxybenzylamino)-2-i-propyl-(2H)pyridazinone;
4-ethyl-5-(4-methoxybenzylamino)-2-i-propyl-3(2H)-pyridazinone;
4-ethyl-5-(3-ethoxybenzylamino)-2-i-propyl-3(2H)-pyridazinone;
4-ethyl-5-(3-ethoxy-4-methoxybenzylamino)-2-i-propyl-(2H)pyridazinone;
4-n-propyl-5-(2,4-dimethoxybenzylamino)-2-i-propyl-3(2H)pyridazinone;
4-n-propyl-5-(3-methoxybenzylamino)-2-i-propyl-3(2H)-pyridazinone;
4-n-propyl-5-(4-methoxybenzylamino)-2-i-propyl-3(2H)-pyridazinone;
4-n-propyl-5-(3-ethoxybenzylamino)-2-i-propyl-3(2H)-pyridazinone;
4-chloro-5-(3,4-diethoxybenzylamino)-2-ethyl-3(2H)-pyridazinone;
4-chloro-5-(3-n-propoxy-4-ethoxybenzylamino)-2-ethyl-3(2H)pyridazinone;
4-chloro-5-(3,4-diethoxybenzylamino)-2-i-propyl-3(2H)pyridazinone

TEST EXAMPLES

A. Anti-allergic activities

A major constituent of SRS-A which is an important mediator for immediate allergy such as bronchoconstriction in bronchial asthma, has already been found to be leukotriene $C_4$ (hereinafter referred to as $LTC_4$), leukotriene $D_4$ (hereinafter referred to as $LTD_4$) or the like. Accordingly, antagonistic activities against SRS-A can be evaluated by any one of the following test methods:

(1) a method of examining the antagonistic activities against SRS-A obtained from a sensitized guinea-pig, (2) a method of examining the antagonistic activities against $LTC_4$, and (3) a method of examining the antagonistic activities against $LTD_4$.

The present inventors examined the antagonistic activities against SRS-A by using the test methods (1) to (3).

Now, the test methods and the results will be described.

Test methods of anti-allergic activities and the results (i) SRS-A antagonism in guinea-pig ileum SRS-A antagonism was determined against the contraction induced by SRS-A in isolated guinea-pig ileum. The SRS-A was prepared in accordance with the method of Brocklehurst (J. Physiol., 151, 416, 1960) and Kohno and Parker (J. Immunol., 125, 446, 1980). Adult male guinea-pigs (200–250 g) were sensitized with chick egg albumin (EA), 100 mg subcutaneously and 100 mg intraperitoneally. Three weeks later the animals were killed by a blow on the head and lungs were perfused free of blood with Tyrode solution passed through the right ventricle. Isolated lungs were chopped into pieces (1 mm$^3$) by a scissors in Tyrode solution and filtrated with gauze, and then 1.0–1.3 g of chopped lung fragments were distributed into individual tubes (9.7 ml of Tyrode solution/tube). EA solution (0.3 ml) at a $3 \times 10^{-4}$ g/ml final concentration was added to the tubes and incubated for 20 min at 37° C., and then the supernatant was used for the SRS-A antagonism.

Assay for SRS-A antagonism was performed as follows: Ileum preparations isolated from male guinea-pig (300–400 g) were suspended under 0.5 g tension in organ baths (5 ml) containing Tyrode solution maintained at 30° C. and gassed with 95% $O_2$+5% $CO_2$. After the repeated responses to histamine ($10^{-7}$ g/ml) was established, the contractile response to SRS-A (0.5 ml) was carried out in the presence of $10^{-6}$ M atropine and $10^{-6}$ M pyrilamine. Test compounds dissolved in 100% dimethyl sulfoxide were added to the organ baths (final concentration of $5\times10^{-7}$ g/ml) 1 min prior to the SRS-A addition, and SRS-A-induced contractions were compared with those of control (SRS-A-induced contraction before the treatment). The SRS-A antagonism (%) = [1.0 - (SRS-A-induced contraction in test compound)/control] × 100

SRS-A antagonism by test compounds ($5\times10^{-7}$ g/ml) are shown in Table 1.

TABLE 1

| Test compound No. | Antagonism (%) | Test compound No. | Antagonism (%) |
|---|---|---|---|
| 1 | 14 | 18 | 74 |
| 2 | 47 | 21 | 77 |
| 3 | 64 | 22 | 76 |
| 4 | 73 | 23 | 18 |
| 5 | 74 | 25 | 81 |
| 9 | 72 | 30 | 53 |
| 10 | 40 | 32 | 18 |
| 11 | 74 | 33 | 41 |
| 12 | 73 | 34 | 19 |
| 16 | 55 | 35 | 10 |
| 44 | 55 | 42 | 14 |
| 38 | 31 | 52 | 72 |
| 41 | 15 | 55 | 12 |
|  |  | FPL-55712 (Reference compound) | 88 |

(ii) $LTC_4$ and $LTD_4$ antagonisms in guinea-pig trachea

Antagonism for $LTC_4$ and $LTD_4$ were determined in isolated guinea-pig trachea prepared as spiral strip. 10 Tracheal preparations were suspended under 1 g tension in ml organ baths and they were incubated for 1 hr prior to use. Contractile responses to $LTC_4$ ($2\times10^{-8}$ g/ml) and $LTD_4$ ($2\times10^{-8}$ g/ml) were obtained after the maximal response to histamine ($10^{-4}$ M). Test compounds dissolved in 100% dimethyl sulfoxide were added to the organ baths (final concentration of $10^{-5}$ g/ml) 5 min prior to $LTC_4$ and $LTD_4$ addition, and then contractile responses to $LTC_4$ and $LTD_4$ were compared with those of control which was obtained from a paired trachea in the absence of test compounds. $LTC_4$- and $LTD_4$-induced contractions were expressed as a percentage of the maximal response to histamine. The antagonism was determined as follows: Antagonism (%)=(1.0−% contraction in test/% contraction in control)×100

$LTC_4$ antagonisms by test compounds ($10^{-5}$ g/ml) are shown in Table 2.

TABLE 2

| Test compound No. | Antagonism (%) | Test compound No. | Antagonism (%) |
|---|---|---|---|
| 2 | 84 | 40 | 17 |
| 3 | 42 | 43 | 57 |
| 4 | 55 | 48 | 30 |
| 5 | 67 | 49 | 8 |
| 6 | 33 | 55 | 14 |
| 10 | 50 | 59 | 17 |
| 11 | 25 | 75 | 100 |
| 12 | 67 | 86 | 100 |
| 14 | 100 | 88 | 81 |
| 15 | 100 | 89 | 89 |
| 16 | 96 | 93 | 93 |
| 21 | 36 | 94 | 83 |
| 22 | 20 | 97 | 100 |
| 24 | 7 | 102 | 97 |
| 29 | 68 | 103 | 100 |
| 30 | 13 | 105 | 100 |
| 32 | 20 | 106 | 100 |
| 33 | 17 | 119 | 100 |
| 35 | 37 | FPL-55712 (Reference compound) | 100 |

$LTD_4$ antagonisms by test compounds ($10^{-5}$ g/ml) are shown in Table 3.

TABLE 3

| Test compound No. | Antagonism (%) | Test compound No. | Antagonism (%) |
|---|---|---|---|
| 3 | 50 | 95 | 62 |
| 54 | 10 | 96 | 59 |
| 13 | 76 | 97 | 100 |
| 15 | 80 | 98 | 55 |
| 14 | 36 | 99 | 99 |
| 17 | 80 | 100 | 21 |
| 39 | 67 | 101 | 54 |
| 58 | 23 | 102 | 86 |
| 50 | 12 | 103 | 100 |
| 56 | 19 | 104 | 68 |
| 57 | 27 | 105 | 100 |
| 8 | 53 | 106 | 100 |
| 6 | 62 | 107 | 65 |
| 7 | 92 | 108 | 53 |
| 60 | 15 | 109 | 92 |
| 46 | 49 | 110 | 69 |
| 45 | 14 | 111 | 72 |
| 36 | 19 | 112 | 86 |
| 26 | 38 | 113 | 40 |
| 28 | 52 | 114 | 77 |
| 53 | 38 | 115 | 73 |
| 61 | 21 | 116 | 89 |
| 20 | 17 | 117 | 25 |
| 19 | 66 | 118 | 61 |
| 47 | 65 | 119 | 100 |
| 74 | 91 | 120 | 26 |
| 75 | 90 | 121 | 31 |
| 76 | 97 | 122 | 23 |
| 77 | 90 | 123 | 88 |
| 78 | 97 | 124 | 71 |
| 79 | 100 | 125 | 53 |
| 80 | 99 | 126 | 63 |
| 81 | 68 | 127 | 76 |
| 82 | 46 | 128 | 21 |
| 83 | 74 | 129 | 48 |
| 84 | 96 | 130 | 100 |
| 85 | 91 | 131 | 52 |
| 86 | 87 | 132 | 61 |
| 87 | 100 | 133 | 66 |
| 88 | 95 | 134 | 75 |
| 89 | 95 | 135 | 61 |
| 90 | 96 | 136 | 64 |
| 91 | 93 | 137 | 96 |
| 92 | 92 | 138 | 86 |
| 93 | 96 | 139 | 57 |
| 94 | 75 | 140 | 77 |
| 141 | 90 | 156 | 72 |
| 142 | 41 | 157 | 88 |
| 143 | 28 | 158 | 99 |
| 144 | 44 | 159 | 98 |
| 145 | 81 | 160 | 98 |
| 146 | 32 | 161 | 95 |
| 147 | 73 | 162 | 100 |
| 148 | 62 | 163 | 95 |
| 149 | 68 | 164 | 82 |
| 150 | 57 | 165 | 71 |
| 151 | 78 | 166 | 100 |
| 152 | 75 | 167 | 96 |
| 153 | 45 | 168 | 99 |
| 154 | 100 | 169 | 100 |
| 155 | 60 |  |  |

TABLE 3-continued

| Test compound No. | Antagonism (%) | Test compound No. | Antagonism (%) |
|---|---|---|---|
| | | FPL-55712 (Reference compound) | 88 |

(iii) Effect on anaphylactic bronchoconstriction in passively sensitized guinea-pig Male guinea-pigs (350–450 g) were passively sensitized with intravenous (i.v.) injection of 0.125 ml rabbit anti-EA serum (Cappel Laboratories) 1 day preceding the experiment. Antigen-induced anaphylactic bronchoconstrictions were measured by modified method of Konzett and Rossler (Arch. Exp. Path. Pharmak., 195, 71, 1940) Sensitized guinea-pigs were anaesthetized with intraperitoneal injection of urethane (1.5 g/kg). The right jugular vein was cannulated for the administration of the all agents and trachea was cannulated to record total pulmonary resistance. Guinea-pigs were artificially ventilated by a small animal respirator (Shinano, Model SN-480-7) set at a stroke volume of 4–5 ml and a rate of 50 breaths per min. The change in pulmonary resistance was measured with a pressure transducer (Nihon Kohden, Model TP-602T) connected to a T-tube on the tracheal cannula. The increase in air overflow volume was expressed as a percentage of the maximum bronchoconstriction obtained by clamping off the trachea. Following surgical preparation, the animals were pretreated with indomethacin (1.0 mg/kg, 10 min), pyrilamine (2 mg/kg, 6 min) and propranolol (0.1 mg/kg, 5 min) prior to the EA challenge (0.1 or 10 mg/kg). All test compounds, 2 mg/kg in 3% Tween 80 or 3% PEG-400, were administered 1 min before the EA challenge. Inhibition (%) of bronchoconstriction was determined as follows Inhibition (%)=(1.0% −maximum bronchoconstriction in test/% maximum bronchoconstriction in control) ×100. The maximum bronchoconstriction was obtain-d within 20 min after the EA challenge and its control value was 73±9% (mean±S.D., n=4). The number of test animals was 2 and the mean inhibition was compared with that of FPL-55712 (Fisons Limited) of the following formula:

In the Table, the dose of EA was 10 mg/kg, and each compound was dissolved or suspended in 3% Tween 80.

TABLE 4-(2)

| Test compound (%) | Solution or suspension for test compound | Inhibition (%) |
|---|---|---|
| 74 | Tween 80 | 31 |
| 75 | Tween 80 | 57 |
| 79 | Tween 80 | 61 |
| 86 | Tween 80 | 29 |
| 87 | Tween 80 | 61 |
| 88 | Tween 80 | 45 |
| 89 | PEG* | 79 |
| 91 | PEG | 73 |
| 97 | Tween 80 | 32 |
| 103 | Tween 80 | 76 |
| 105 | Tween 80 | 29 |
| 106 | Tween 80 | 65 |
| 109 | Tween 80 | 30 |
| 112 | Tween 80 | 49 |
| 119 | Tween 80 | 33 |
| EPL-55712 | Tween 80 | 60 |

In the Table, the dose of EA was 0.1 mg/kg.
*: PEG represents polyethylene glycol-400.

(iv) Effect on bronchoconstriction induced by intravenous (i.v.) administration of LTD$_4$ Bronchoconstrictions induced by i.v. administration of LTD$_4$ in guinea-pigs (350–450 g) were measured as described in anaphylactic bronchoconstriction. Guinea-pigs were anaesthetized with urethane (1.5 g/kg) and the trachea was cannulated to record total pulmonary resistance. The right jugular vein was cannulated for the administration of the all agents. The guinea-pigs were artificially ventilated by a small respirator set at a stroke volume of 5 ml and a rate of 50 breaths per min. LTD$_4$ (2 μg/kg)-induced bronchoconstriction was shown by the increase in air overflow volume. After the response to histamine (5 μg/kg) was checked, the first response to LTD$_4$ was obtain-d as control. Test compounds, 2 mg/kg in Tween 80, were administered 2 min prior to the second response to LTD$_4$, because there was no difference between the first response and the second response to LTD$_4$. Inhibition (%) of the bron-

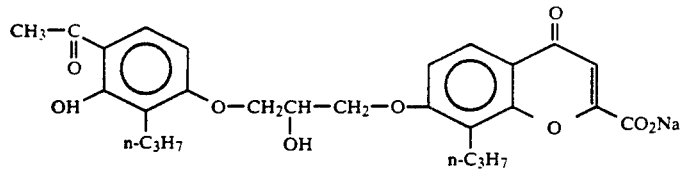

Effect of the test compounds (2 mg/kg, i.v.) are shown in Table 4-(1) and 4-(2).

TABLE 4-(1)

| Test compound No. | Inhibition (%) | Test compound No. | Inhibition (%) |
|---|---|---|---|
| 2 | 21 | 52 | 30 |
| 9 | 35 | 43 | 14 |
| 10 | 31 | 13 | 43 |
| 11 | 21 | 15 | 56 |
| 14 | 28 | 53 | 38 |
| 22 | 23 | | |
| 44 | 72 | FPL-55712 (Reference compound) | 27 | choconstriction was determined as follows: Inhibition (%) =(1.0 −peak value in the second response/peak value in the first response)×100. Results in all of the experiments were compared with those of FPL-55712 (Fisons Limited).

Effect of the test compounds (2 mg/kg, i.v.) are shown in Table 5.

TABLE 5

| Test compound No. | Inhibition (%) |
|---|---|
| 1 | 23 |
| 3 | 60.6 |
| 9 | 38 |
| 44 | 72.5 |

TABLE 5-continued

| Test compound No. | Inhibition (%) |
|---|---|
| FPL-55712 | 100 |

B. Acute toxicity test

(i) Test method-(1)

The lethal ratio was determined in ddY strain male mice (4 weeks old) at 7 days after the oral administration of test compounds. The results are shown in Table 6.

TABLE 6

| | Dose (300 mg/kg. P.O.) |
|---|---|
| Test compound No. | Lethal ratio |
| 10 | 0/3 |
| 4 | 0/3 |

(ii) Test method-(2)

The lethal ratio was determined in ddY strain male (4 weeks old) at 7 days after the intraperitoneal injection of test compounds. The results are shown in Table 7.

TABLE 7

| Test compound No. | Dose (mg/kg) | Lethal ratio (Death number/Experimental number) |
|---|---|---|
| 75 | 100 | 0/2 |
| 76 | 200 | 0/2 |
|  | 400 | 0/1 |
| 77 | 200 | 0/2 |
|  | 400 | 0/2 |
| 78 | 200 | 0/2 |
|  | 400 | 0/1 |
| 79 | 200 | 0/2 |
| 80 | 200 | 0/2 |
|  | 400 | 0/1 |
| 86 | 200 | 0/2 |
|  | 400 | 0/1 |
| 87 | 200 | 0/2 |
|  | 400 | 0/2 |
| 88 | 200 | 0/2 |
|  | 400 | 0/2 |
| 89 | 200 | 0/2 |
|  | 400 | 0/1 |
| 90 | 200 | 0/2 |
|  | 400 | 0/2 |
| 91 | 100 | 0/2 |
| 94 | 200 | 0/2 |
| 97 | 200 | 0/2 |
|  | 400 | 0/1 |
| 99 | 100 | 0/2 |
| 102 | 100 | 0/2 |
| 103 | 200 | 0/2 |
| 105 | 100 | 0/2 |
| 106 | 200 | 0/2 |
|  | 400 | 0/1 |

From these results, it is evident that the compounds of the present invention produce prominent effects on the angtagonism for SRS-A and its major constituents $LTC_4$ and $LTD_4$ in vitro and in vivo. Therefore, the compounds of the present invention are proved to be useful for prophylactic and therapeutic drugs in SRS-A-induced various allergic diseases, for example bronchial asthma, allergic rhinitics and urticaria.

As the manner of administration of the compounds of the present invention, there may be mentioned a non-oral administration by injection (subcutaneous, intravenous, intramuscular or intraperitoneal injection), an ointment, a suppository or an aerosol, or an oral administration in the form of tablets, capsules, granules, pills, sirups, liquids, emulsions or suspensions.

The above pharmacological or veterinary composition contains a compound of the present invention in an amount of from about 0.1 to about 99.5% by weight, preferably from about 0.5 to about 95% by weight, based on the total weight of the composition. To the compound of the present invention or to the composition containing the compound of the present invention, other pharmacologically or veterinarily active compounds may be incorporated. Further, the composition of the present invention may contain a plurality of compounds of the present invention.

The clinical dose of the compound of the present invention varies depending upon the age, the body weight, the sensitivity or the symptom, etc. of the patient. However, the effective daily dose is usually from 0.003 to 1.5 g, preferably from 0.01 to 0.6 g, for an adult. However, if necessary, an amount outside the above range may be employed.

The compounds of the present invention may be formulated into various suitable formulations depending upon the manner of administration, in accordance with conventional methods commonly employed for the preparation of pharmaceutical formulations.

Namely, tablets, capsules, granules or pills for oral administration, may be prepared by using an excipient such as sugar, lactose, glucose, starch or mannitol; a binder such as sirups, gum arabic, gelatin, sorbitol, tragacant gum, methyl cellulose or polyvinylpyrrolidone; a disintegrant such as starch, carboxymethyl cellulose or its calcium salt, crystal cellulose powder or polyethylene glycol; a gloss agent such as talc, magnesium or calcium stearate or colloidal silica; or a lubricant such as sodium laurate or glycerol. The injections, solutions, emulsions, suspensions, sirups or aerosols, may be prepared by using a solvent for the active ingredient such as water, ethyl alcohol, isopropyl alcohol, propylene glycole, 1,3-butylene glycol, or polyethylene glycol; a surfactant such as a sorbitol fatty acid ester, a polyoxyethylene sorbitol fatty acid ester, a polyoxyethylene fatty acid ester, a polyoxyethylene ether of hydrogenated caster oil or lecithin; a suspending agent such as a sodium salt of carboxymethyl, a cellulose derivative such as methyl cellulose, or a natural rubber such as tragacant gum or gum arabic; or a preservative such as a paraoxy benzoic acid ester, benzalkonium chloride or a salt of sorbic acid. Likewise, the suppositories may be prepared by using e.g. polyethylene glycol, lanolin or cocoa butter.

Now, the present invention will be described in detail with reference to Examples. However, it should be understood that the present invention is by no means restricted by these specific Examples. In Examples or in Reference Examples, the symbols "NMR" and "MS" indicate "nuclear magnetic resonance spectrum" and "mass spectrometry". In the NMR data, only the characteristic absorptions are given. Likewise, in the MS data, only the principal peaks or typical fragment peaks are given.

In this specification, "Me" means a methyl group, "Et" an ethyl group, "Pr" a propyl group, "Bu" a butyl group, and "Ph" a phenyl group. Likewise, a "n" indicates "normal", "i" indicates "iso", and "t" indicates "tertiary".

REFERENCE EXAMPLE 1

3,4-Dimethoxybenzylamine hydrochloride

A mixture comprising 24.06 g of 3,4-dimethoxybenzaldehyde, 14.28 g of hydroxylamine sulfate, 7.25 g of sodium hydroxide, 300 ml of methanol and 250 ml of water, was refluxed under stirring for one hour. After cooling, 14.5 g of sodium hydroxide was added and dissolved in the mixture, and then 40 g of Raney nickel (Ni-Al alloy) was gradually added under cooling with ice. After the completion of the addition, the ice bath was removed, and the mixture was continuously stirred at room temperature for one hour. The reaction mixture was filtered, and methanol in the filtrate was distilled off under reduced pressure, and the residue was extracted with diethyl ether. The extract was washed with a saturated sodium chloride aqueous solution, and dried over sodium sulfate, and then the solvent was distilled off to obtain a colorless oily substance.

NMR(CDCl$_3$)$\delta$: 6.77 (3H, s), 3.81, 3.80 (each 3H, s), 3.75 (2H, s), 1.58 (2H, s, disappeared upon the addition of D$_2$O).

The residual oily substance was diluted with 100 ml of diethyl ether, and 25 ml of a 1,4-dioxane solution of 6N HCl was added thereto under cooling with ice. The precipitated solid substance was collected by filtration, and washed with ether to obtain 29.36 g of the above identified compound as a colorless powder.

In a similar manner as above, benzylamines having different substituents, i.e. 4-ethyl, 4-i-propyl, 3-methyl-4-methoxy, 3-methoxy, 4-ethoxy, 4-n-propoxy, 3,4-methylenedioxy, 3-amyloxy-4-methoxy and 4-cyano, and their hydrochlorides were prepared, respectively, from the corresponding benzaldehydes.

REFERENCE EXAMPLE 2

4-Diethylaminobenzylamine hydrochloride

A mixture of 8.80 g of 4-diethylaminobenzaldehyde, 4.59 g of O-methylhydroxylamine hydrochloride, 11.87 g of pyridine and 80 ml of ethanol was refluxed under stirring for one hour. The solvent was distilled off under reduced pressure, and water was added to the residue. The mixture was extracted with benzene. The extract was washed with water (twice) and a saturated sodium chloride aqueous solution, and dried over sodium sulfate, and then the solvent was distilled off to obtain 10.30 g of O-methylaldoxime as a pale yellow oily substance.

NMR(CDCl$_3$)$\delta$:7.87 (1H, s), 7.34, 6.54 (each 2H, ABq), 3.85 (3H, s), 3.33 (4H, q), 1.15 (6H, t).

Into a suspension comprising 7.6 g of sodium borohydride and 200 ml of tetrahydrofuran, a solution obtained by dissolving 22.8 g of trifluoroacetic acid in 10 ml of tetrahydrofuran, was dropwise added over a period of 20 minutes under stirring and cooling with ice. After the completion of the dropwise addition, the ice bath was removed, and the reaction solution was stirred at room temperature for one hour, and then 10.30 g of the above obtained o-methylaldoxime was added thereto. The reaction was conducted at the same temperature for one hour, and then the mixture was refluxed for two hours. After cooling, water was added to the reaction mixture under cooling with ice to decompose the excess reducing agent. Tetrahydrofuran was distilled off, and the residue thereby obtained was extracted with dichloromethane. The extract was washed with water and a saturated sodium chloride aqueous solution, and dried over sodium sulfate, and then the solvent was distilled off. Then, 25 ml of a dioxane solution of 6N HCl was added to the residue under cooling with ice. The mixture was subjected to distillation under reduced pressure. The solid substance thereby obtained was treated with methanol-ether to obtain 11.13g of the above identified compound as a colorless powder. The NMR spectrum of the free amine is as follows:

NMR(CDCl$_3$)$\delta$: 7.06, 6.56 (each 2H, ABq), 3.66 (2H, s), 3.27 (4H, q), 1.55 (2H, s, disappeared upon the addition of D$_2$O), 1.11 (6H, t).

In the same manner as above, benzylamines having various substituents, i.e. 4-morpholino and 4-methylmercapto, and their hydrochlorides, were prepared, respectively, from the corresponding benzaldehydes.

REFERENCE EXAMPLE 3

4-(2-Carboxy-trans-ethenyl)benzylamine

Into a mixture of 0.946 g of sodium borohydride and 100 ml of tetrahydrofuran, a mixed solution of 2.850 g of trifluoroacetic acid and 20 ml of tetrahydrofuran, was dropwise added under stirring and cooling with ice. After the completion of the dropwise addition, the ice bath was removed, and the reaction mixture was stirred for one hour. Then, a solution obtained by dissolving 4.325 g of 4-cyanociannamic acid obtained by heating and condensing 4-cyanobenzaldehyde with malonic acid in pyridine in the presence of a catalytic amount of piperidine, in 140 ml of tetrahydrofuran and 30 ml of 1,4-dioxane, was dropwise added to the reaction mixture, and stirred at room temperature for 2.5 hours. After cooling, ice pieces were added to decompose the excess reducing agent. Then, the reaction mixture was concentrated, and the precipitated powder was collected by filtration and subjected to vacuum drying to obtain 3.50 g of the above identified compound as a colorless powder.

REFERENCE EXAMPLE 4

4-Chlorobenzylamine hydrochloride

Into a mixture comprising 7.30 g of sodium borohydride, 6.00 g of 4-chlorobenzamide and 100 ml of 1,4-dioxane, a mixed solution of 11.58 g of acetic acid and 30 ml of 1,4-dioxane, was dropwise added under stirring and cooling with ice over a period of 30 minutes. After the dropwise addition, the reaction mixture was refluxed under stirring for two hours. After cooling, ice pieces were gradually added to decompose the excess reducing agent, and the solvent was distilled off under reduced pressure Then, the residue was extracted with chloroform. The extract was washed with a saturated sodium chloride aqueous solution, and dried over sodium sulfate, and then the solvent was distilled off to a concentration of about 80 ml. The concentrated solution was cooled with ice, and 10 ml of a dioxane solution of 6N HCl was dropwise added thereto The precipitated solid substance was treated with methanol-ether to obtain 3.16 g of the above identified compound as a colorless powder The NMR spectrum of the free amine is as follows:

NMR(CDCl$_3$)$\delta$: 7.38 (4H, s), 4.16 (2H, s), 1.55 (2H, s, disappeared upon the addition of D$_2$O).

REFERENCE EXAMPLE 5

4-Dimethylaminocarbonylbenzylamine hydrochloride

Into a mixture comprising 7 g of 4-carboxy-N-t-butoxycarbonylbenzylamine obtained by reacting 4- aminomethylbenzoic acid with di-t-butyl dicarbonate in the presence of sodium hydroxide in a usual manner, 6.36 g of triethylamine and 150 ml of dichloromethane, 4.14 g of ethyl chloroformate was gradually added under stirring and cooling with ice. After the completion of the dropwise addition, the mixture was stirred under cooling with ice for one hour, and 2.51 g of dimethylamine hydrochloride was added thereto at the same temperature. The ice bath was removed, and the reaction solution was stirred at room temperature for 30 minutes. The reaction solution was washed successively with an aqueous sodium hydrogencarbonate solution, water, a 10% citric acid aqueous solution and water, and dried over sodium sulfate, and then the solvent was distilled off. The residue thereby obtained was subjected to silica gel column chromatography (developer; CHCl$_3$:MeOH =19:1, v/v) to obtain 3.22 g of 4-dimethylaminocarbonyl-N-t-butoxycarbonylbenzylamine as a yellow oily substance.

NMR(CDCl$_3$)δ: 7.28 (4H, s), 4.28 (2H, d), 3.01 (6H, s) 1.44 (9H, s).

3.22 g of the above obtained 4-dimethylaminocarbonyl-N-t-butoxycarbonylbenzylamine was dissolved in 5 ml of methanol, and 10 ml of a dioxane solution of 6N HCl was added thereto, and then the mixture was left to stand still overnight. The mixture was subjected to distillation under reduced pressure. The solid substance thereby obtained was treated with methanol-ether to obtain 2.6 g of the above identified compound as a colorless powder. The NMR spectrum of the free amine is as follows:

NMR(CDCl$_3$)δ: 7.31 (4H, s), 3.82 (2H, s), 3.00 (6H, s), 1.63 (2H, s).

In a similar manner as above, benzylamines having different substituents, i.e. 4-diethylaminocarbonyl, 4-di-n-propylaminocarbonyl, 4-(4-methylpiperazinylcarbonyl), 4-(4-ethylpiperazinylcarbonyl) and 4-morpholinocarbonyl, and their hydrochlorides were prepared, respectively, from the corresponding 4-aminocarbonyl-N-t-butoxycarbonylbenzylamine.

REFERENCE EXAMPLE 6

4-Dimethylaminomethylbenzylamine

Into a suspension of 0.95 g of lithium aluminum hydride and 100 ml of tetrahydrofuran, a solution obtained by dissolving 1.77 g of 4-dimethylaminocarbonylbenzylamine prepared in Reference Example 5 in 50 ml of tetrahydrofuran, was dropwise added under stirring, and the reaction solution was refluxed for 3 hours. After cooling, the reaction solution was cooled with ice, and ice pieces were gradually added to decompose the excessive reducing agent. Tetrahydrofuran was distilled off, and the residue thereby obtained was extracted with dichloromethane. The extract was washed with water and a saturated sodium chloride aqueous solution, and dried over sodium sulfate, and then the solvent was distilled off to obtain 1.13 g of the above identified compound as a pale yellow oily substance.

NMR(CDCl$_3$)δ: 7.23 (4H, s), 3.82 (2H, s), 3.39 (2H, s), 2.21 (6H, s), 1.51 (2H, s, disappeared upon the addition of D$_2$O).

In a similar manner as above, benzylamines having different substituents, i.e. 4-diethylaminomethyl, 4-(4-methylpiperazinylmethyl), 4-(4-ethylpiperazinylmethyl) and 4-morpholinomethyl were prepared, respectively, from the corresponding benzylamines prepared in Reference Example 5.

REFERENCE EXAMPLE 7

4-Di-n-propylaminomethyl-N-methylbenzylamine

Into a mixture of 1.31 g of lithium aluminum hydride and 50 ml of tetrahydrofuran, a solution obtained by dissolving 2.88 g of 4-di-n-propylaminocarbonyl-N-t-butoxycarbonylbenzylamine prepared in Reference Example 5 in 70 ml of tetrahydrofuran, was dropwise added under stirring at room temperature. After the completion of the dropwise addition, the mixture was refluxed for 3 hours. After cooling, ice pieces were gradually added to the mixture under cooling with ice to decompose the excessive reducing agent. Tetrahydrofuran was distilled off under reduced pressure, and the residue was extracted with chloroform. The extract was washed with water, and dried over sodium sulfate, and then the solvent was distilled off to obtain 1.30 g of the above identified compound as a pale yellow oily substance.

NMR(CDCl$_3$)δ: 7.25 (4H, s), 3.71 (2H, s), 3.51 (2H, s), 2.43 (3H, s), 1.86 (6H, t).

In a similar manner as above, 4-methyl-N-methylbenzylamine and 3-methoxy-N-methylbenzylamine were prepared, respectively, from 4-methyl-N-ethoxy-carbonylbenzylamine and 3-methoxy-N-ethoxycarbonylbenzylamine.

REFERENCE EXAMPLE 8

4-Methyl-5-chloro-2-t-butyl-3(2H)pyridazinone

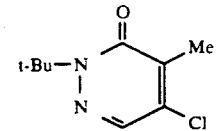

To 7.2 g of metal magnesium in 10 ml of dried ethyl ether, 33.5 g (0.25 mol) of methyl iodide was dropwise added in a nitrogen stream to prepare a Grignard reagent. After the completion of the dropwise addition of methyl iodide, 1000 ml of dried toluene was added to the mixture. The solution was heated to a temperature of from 60° to 70° C., and methyl iodide was further added until magnesium was completely dissolved. The Grignard reagent was cooled to room temperature, and a solution obtained by dissolving 22.1 g (0.1 mol) of 2-t-butyl-4,5-dichloro-3(2H)pyridazinone in 200 ml of dried toluene, was dropwise added over a period of 20 minutes. After the completion of the dropwise addition, the mixture was reacted at room temperature for 1.5 hours, and a mixed solution of 100 ml of concentrated hydrochloric acid and 900 ml of ice water was poured in the reaction solution for liquid separation. Then, the organic layer was washed with 500 ml of 10% sodium hydroxide and 500 ml of water, and dried over anhydrous sodium sulfate, and then the solvent was distilled off under reduced pressure to obtain 17. 2 g of a crude product. This crude product was subjected to distillation (boiling point: 60°-62° C./0.22 mmHg), and separated and purified by silica gel column chromatography (developer; hexane:acetone =15:1) to obtain 4.5 g of 2-t-butyl-5-chloro-4-methyl-3(2H)-pyridazinone.

$n_D^{20}$=1.5238

NMR(CDCl$_3$)δ: 1.63 (9H, s), 2.23 (3H, s), 2.66 (1H, s),

REFERENCE EXAMPLE 9

4-Ethyl-5-chloro-2-t-butyl-3(2H)pyridazinone

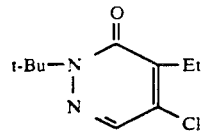

Into a four-necked flask of 1 liter, 43 g of ethylmagnesium bromide (3 mol/liter of an ether solution) and 200 ml of dehydrated toluene were charged. While thoroughly stirring the mixture at room temperature, 22.1 g (0.1 mol) of 2-t-butyl-4,5-dichloro-3(2H)pyridazinone was added in three portions. The reaction temperature was raised to a level of about 60° C., and the stirring was continued for about 30 minutes. The disappearance of the starting dichloropyridazinone was confirmed by thin layer chromatography (developer; hexane:acetone =20:1, v/v), whereupon the reaction was terminated. After the addition of about 300 ml of chilled water, the mixture was stirred vigorously, and transferred to a separating funnel, and then the aqueous layer was removed. The organic layer was washed with about 200 ml of water, and dried over anhydrous sodium sulfate, and then the solvent was distilled off. The pale brown oily substance thereby obtained was purified by silica gel column chromatography (developer; benzene) to obtain pale yellow crystals. 1.45 g (yield: 67.6%).

mp: 61.5–62.5° C.

NMR(CDCl$_3$)δ:7.62 (1H, s), 2.72 (2H, q), 1.61 (9H, s), 1.14 (2H, t).

REFERENCE EXAMPLE 10

4-n-Propyl-5-chloro-2-t-butyl-3(2H)pyridazinone

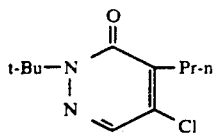

The desired product was obtained in the same manner as in Reference Example 9 except that the starting ethylmagnesium chloride used in Reference Example 9 was replaced by n-propylmagnesium chloride.

NMR(CDCl$_3$)δ: 7.64 (1H, s), 2.70 (2H, q), 1.66 (2H, m), 1 62 (9H, s), 0.98 (3H, t).

mp: 45° C.

REFERENCE EXAMPLE 11

4-Ethyl-5-chloro-2-ethyl-3(2H)pyridazinone

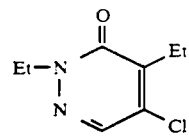

The desired product was obtained as a pale yellow oil in the same manner as in Reference Example 9 except that the starting 2-t-butyl-4,5-dichloro-3(2H)pyridazinone used in Reference Example 9 was replaced by 2-ethyl-4,5-dichloro-3(2H)pyridazinone.

NMR(CDCl$_3$)δ: 7.68 (1H, s), 4.18 (2H, q), 2.75 (2H, q), 1.35 (3H, t).

EXAMPLE 1

4-Chloro-5-(3,4-dimethoxybenzylamino)-2-n-propyl-3-(2H)pyridazinone (Compound No. 14)

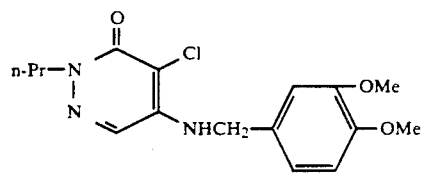

A mixture comprising 1.52 g of 3,4-dimethoxybenzylamine hydrochloride prepared in Reference Example 1, 0.62 g of 4,5-dichloro-2-n-propyl-3(2H)pyridazinone, 1.66 g of potassium carbonate, 10 ml of 1,4-dioxane and 30 ml of water was refluxed under stirring for 5 hours. The solvent was distilled off under reduced pressure, and water was added to the residue thereby obtained, and the mixture was extracted with ethyl acetate. The extract was washed successively with 2% diluted hydrochloric acid, water and a saturated sodium chloride aqueous solution, and dried over sodium sulfate, and then the solvent was distilled off to obtain a pale yellow oily substance. This substance was crystallized from diethyl ether-n-hexane to obtain 522 mg of the above identified compound having a melting point of from 139 to 140° C. as colorless crystals.

IR ($\nu_{KBrmax}$) cm$^{-1}$ 3300, 1635 (shoulder), 1605, 1525.

NMR(CDCl$_3$)δ: 7.47 (1H, s), 6.65–6.87 (3H, m), 5.03 (1H, broad s), 4,47, 4.37 (total 2H, each s), 4.04 (2H, t), 3.82 (6H, s), 2.0–1.5 (2H, m), 0.91 (3H, t).

MS (m/e): 337(M$^+$), 302, 151 (100%).

The compounds as identified in Table 8 were prepared in the synthetic manner and after-treatment similar to those in Example 1 except that the benzylamine hydrochlorides with Y$_1$, Y$_2$, Y$_3$ and R$_3$ as identified in Table 8 were used instead of the starting 3,4-dimethoxybenzylamine hydrochloride used in Example 1, and the 4,5-di-(chloro or bromo-)-2-alkyl3(2H)pyridazinones with R$_1$ and R$_2$ as identified in Table 8 were used instead of the starting 4,5-dichloro-2-n-propyl-3(2H)pyridazinone. In the NMR data, only the characteristic absorptions are given in Table 8.

TABLE 8

Synthesis of 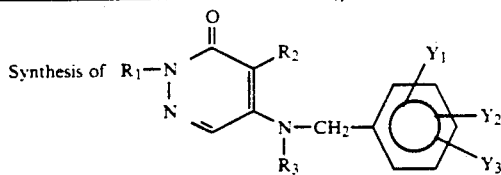

| Compound No. | $R_1$ | $R_2$ | $R_3$ | $Y_1$ | $Y_2$ | $Y_3$ | mp(°C.) | NMR (CDCl$_3$)δ | MS (m/e) |
|---|---|---|---|---|---|---|---|---|---|
| 1 | t-Bu | Cl | H | H | H | H | 151.5–152.5 | 7.51(1H, s), 4.60, 4.50(total 2H, each s), 1.61(9H, s) | |
| 2 | t-Bu | Cl | H | 3-Me | H | H | 155 | 7.48(1H, s), 4.51, 4.41(total 2H, each s), 2.36(3H, s), 1.61(9H, s) | |
| 3 | t-Bu | Cl | H | 4-Me | H | H | 169.5–171.5 | 7.50(1H, s), 4.51, 4.41(total 2H, each s), 2.36(3H, s), 1.60(9H, s) | |
| 4 | t-Bu | Cl | H | 4-Et | H | H | 138 | 7.51(1H, s), 4.51, 4.41(total 2H, each s), 1.61(9H, s), 1.22(3H, t) | |
| 5 | t-Bu | Cl | H | 4-i-Pr | H | H | 148 | 7.45(1H, s), 4.48, 4.38(total 2H, each s), 1.61(9H, s), 1.23(6H, d) | |
| 6 | Et | Cl | H | 3-OMe | H | H | 120 | 7.57(1H, s), 4.58, 4.48(total 2H, each s), 3.81(3H, s), 1.34(3H, t) | 293(M$^+$), 121(100%) |
| 7 | i-Pr | Cl | H | 3-OMe | H | H | 148–150 | 7.56(1H, s), 4.54, 4.45(total 2H, each s), 3.79(3H, s), 1.29(6H, d) | 307(M$^+$), 121(100%) |
| 8 | t-Bu | Cl | H | 3-OMe | H | H | 180–182 | 7.47(1H, s), 4.54, 4.44(total 2H, each s), 3.79(3H, s), 1.61(9H, s) | 321(M$^+$), 121(100%) |
| 9 | t-Bu | Cl | H | 4-OMe | H | H | 141–142 | 7.52(1H, s), 4.51, 4.41(total 2H, each s), 3.80(3H, s), 1.61(9H, s) | |
| 10 | t-Bu | Cl | H | 4-OEt | H | H | 124 | 7.42(1H, s), 4.42, 4.32(total 2H, each s), 1.60(9H, s), 1.38(3H, t) | |
| 11 | t-Bu | Cl | H | 4-O—Pr-n | H | H | 129–132 | 7.51(1H, s), 4.49, 4.39(total 2H, each s), 1.61(9H, s), 1.02(3H, t) | |
| 12 | t-Bu | Cl | H | 3-Me | 4-OMe | H | 168–170 | 7.47(1H, s), 4.43, 4.33(total 2H, each s), 3.79(3H, s), 2.20(3H, s), 1.60(9H, s) | |
| 13 | Et | Cl | H | 3-OMe | 4-OMe | H | 116–117 | 7.48(1H, s), 4.47, 4.38(total 2H, each s), 3.83(6H, s), 1.32(3H, t) | 323(M$^+$), 151(100%) |
| 15 | i-Pr | Cl | H | 3-OMe | 4-OMe | H | 118–119 | 7.51(1H, s), 4.47, 4.37(total 2H, each s), 3.81(6H, s), 1.24(6H, d) | 337(M$^+$), 151(100%) |
| 16 | t-Bu | Cl | H | 3-OMe | 4-OMe | H | 156–157 | 7.44(1H, s), 4.46, 4.36(total 2H, each s), 3.84(6H, s), 1.60(9H, s) | |
| 17 | t-Bu | Br | H | 3-OMe | 4-OMe | H | 173–175 | 7.37(1H, s), 4.47, 4.38(total 2H, each s), 3.85(6H, s), 1.60(9H, s) | 395(M$^+$), 151(100%) |
| 18 | t-Bu | Cl | H | 3-O\4-O (methylenedioxy) | | H | 162–164 | 7.39(1H, s), 5.89(2H, s), 4.41, 4.31(total 2H, each s), 1.60(9H, s) | 335(M$^+$), 135(100%) |
| 19 | Et | Cl | H | 3-O—C$_5$H$_{11}$-n | 4-OMe | H | 113 | 7.57(1H, s), 4.49, 4.39(total 2H, each s), 3.87(3H, s) | 378(M$^+$), 207(100%) |
| 20 | t-Bu | Cl | H | 3-O—C$_5$H$_{11}$-n | 4-OMe | H | 117 | 7.50(1H, s), 4.46, 4.36(total 2H, each s), 3.83(3H, s), 1.61(9H, s) | 407(M$^+$), 207(100%) |
| 21 | t-Bu | Cl | H | 4-SMe | H | H | 171–171.5 | 7.49(1H, s), 4.49, 4.39(total 2H, each s), 2.45(3H, s), 1.59(9H, s) | 337(M$^+$), 137(100%) |
| 22 | t-Bu | Cl | H | 4-Cl | H | H | 152.5–153 | 7.45(1H, s), 4.51, 4.41(total 2H, each s), 1.59(9H, s) | 325(M$^+$), 125(100%) |
| 23 | t-Bu | Cl | H | 4-CO$_2$H | H | H | 239–241 | (CDCl$_3$+DMSO-d$_6$): 7.37(1H, s), 4.65, 4.55(total 2H, each s), 1.57(9H, s) | 335(M$^+$), 135(100%) |
| 24 | t-Bu | Cl | H | 4-CH=CH-CO$_2$H | H | H | 259–261 | (CDCl$_3$+DMSO-d$_6$): 7.45, 6.36(each 1H, ABq, J=16Hz), 4.55, 4.44(total 2H, each s), 1.49(9H, s) | 361(M$^+$), 161(100%) |
| 63 | i-Pr | Cl | H | 4-CO$_2$H | H | H | 238–240 | (CDCl$_3$+DMSO-d$_6$): 7.94, 7.33(each 2H, ABq), 4.65, 4.55(total 2H, each s), 1.26(6H, d) | 321(M$^+$), 135(100%) |
| 72 | t-Bu | Cl | H | 4-CN | H | H | 135.5–136 | 7.63, 7.42(each 2H, ABq), 7.30(1H, s), 4.65, 4.55(total 2H, each s), 1.58(9H, s) | 316(M$^+$), 116(100%) |

EXAMPLE 2

4-Chloro-5-(4-dimethylaminobenzylamino)-2-t-butyl-3(2H)-pyridazinone (Compound No. 25)

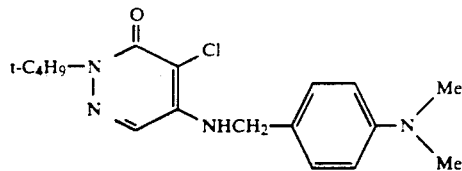

A mixture comprising 2.81 g of 4-dimethylaminobenzylamine dihydrochloride, 1.55 g of 4,5-dichloro-2-t-butyl-3(2H)pyridazinone, 3.87 g of potassium carbonate, 30 ml of 1,4-dioxane and 10 ml of water was refluxed under stirring for 15 hours. The solvent was distilled off under reduced pressure, and water was added to the residue thereby obtained, and the mixture was extracted with benzene. The extract was washed with water and a saturated sodium chloride aqueous solution, and dried over sodium sulfate, and then the solvent was distilled off to obtain a pale yellow solid substance. This substance was subjected to silica gel column chromatography, and eluted with benzene-ethyl acetate (5:1, v/v). The colorless solid substance thereby obtained was crystallized from benzene-n-hexane to obtain 1.20 g of the above identified compound having a melting point of from 168 to 169° C. as colorless crystals.

IR ($\nu_{KBrmax}$) cm$^{-1}$ 3300, 1630 (shoulder), 1600, 1520.

NMR(CDCl$_3$)δ: 7.46 (1H, s), 7.09, 6.63 (each 2H, ABq), 4.85 (1H, broad s), 4.38, 4.29 (total 2H, each s), 2.90 (6H, s), 1.60 (9H, s)

MS (m/e): 334(M+), 299, 243, 134 (100%).

The compounds as identified in Table 9 were prepared in the synthetic manner and after-treatment similar to those in Example 2 except that the benzylamine dihydrochlorides with $Y_1$, $Y_2$, $Y_3$ and $R_3$ as identified in Table 9 were used instead of the starting 4-dimethylaminobenzylamine dihydrochloride used in Example 2, and the 4,5-di(chloro or bromo)-2-alkyl-3(2H)pyridazinones with $R_1$ and $R_2$ as identified in Table 8 were used instead of the starting 4,5-dichloro-2-t-butyl-3(2H)pyridazinone. In the NMR data, only the characteristic absorptions are given in Table 9.

TABLE 9

Synthesis of

| Compound No. | $R_1$ | $R_2$ | $R_3$ | $Y_1$ | $Y_2$ | $Y_3$ | mp(°C.) | NMR (CDCl$_3$)δ | MS (m/e) |
|---|---|---|---|---|---|---|---|---|---|
| 26 | i-Pr | Cl | H | 4-N(Me)$_2$ | H | H | 161–162.5 | 7.59(1H, d), 4.41, 4.31(total 2H, each s), 2.91(6H, s), 1.29(6H, d) | 320(M⁻), 134(100%) |
| 27 | Et | Cl | H | 4-N(Me)$_2$ | H | H | 143.5–144 | 7.41(1H, s), 4.40, 4.30(total 2H, each s), 2.90(6H, s), 1.31(3H, t) | 306(M⁻), 134(100%) |
| 28 | t-Bu | Br | H | 4-N(Me)$_2$ | H | H | 155–156 | 7.40(1H, s), 4.40, 4.30(total 2H, each s), 2.91(6H, s), 1.60(9H, s) | 378(M+), 134(100%) |
| 29 | t-Bu | Cl | H | 4-N(Et)$_2$ | H | H | 133.5–134 | 7.49(1H, s), 4.37, 4.27(total 2H, each s), 1.60(9H, s), 1.15(3H, t) | 362(M⁻), 162(100%) |
| 30 | t-Bu | Cl | H | 4-N(morpholino) | H | H | 163–164 | 7.42(1H, d), 4.42, 4.32(total 2H, each s), 1.59(9H, s) | 376(M+), 176(100%) |
| 31 | t-Bu | Cl | H | 4-CH$_2$N(Me)$_2$ | H | H | Viscous oily substance | 7.48(1H, s), 4.56, 4.46(total 2H, each s), 2.35(6H, s), 1.61(9H, s) | 348(M+), 249(100%) |
| 32 | t-Bu | Cl | H | 4-CH$_2$N(Et)$_2$ | H | H | Viscous oily substance | 7.49(1H, s), 4.56, 4.46(total 2H, each s), 1.60(9H, s), 1.07(6H, t) | 376(M+), 361 |
| 33 | t-Bu | Cl | H | 4-CH$_2$N(morpholino) | H | H | 135 | 7.46(1H, s), 4.53, 4.43(total 2H, each s), 3.47(2H, s), 1.59(9H, s) | 390(M+), 249(100%) |
| 34 | t-Bu | Cl | H | 4-CH$_2$N(N-Me piperazino) | H | H | Viscous oily substance | 7.49(1H, s), 4.54, 4.44(total 2H, each s), 2.47(8H, s), 2.38(3H, s), 1.61(9H, s) | 403(M+), 202(100%) |
| 35 | t-Bu | Cl | H | 4-CH$_2$N(N-Et piperazino) | H | H | Viscous oily substance | 7.49(1H, s), 4.57, 4.47(total 2H, each s), 2.48(8H, s), 1.60(9H, s), 1.08(3H, t) | 417(M+), 216(100%) |

EXAMPLE 3

4Chloro-5-(4-dimethylaminocarbonylbenzylamino)2-t-butyl-3(2H)pyridazinone (Compound No. 37)

with $Y_1$, $Y_2$, $Y_3$ and $R_3$ as identified in Table 10 were used instead of the starting 4-dimethylaminocarbonylbenzylamine used in Example 3. In the NMR data, only the characteristic absorptions are shown in Table 10.

TABLE 10

Synthesis of

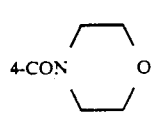

| Compound No. | $R_1$ | $R_2$ | $R_3$ | $Y_1$ | $Y_2$ | $Y_3$ | mp(°C.) | NMR (CDCl$_3$)δ | MS (m/e) |
|---|---|---|---|---|---|---|---|---|---|
| 38 | t-Bu | Cl | H | 4-CON(Et)$_2$ | H | H | Viscous oily substance | 7.43(1H, s), 4.60, 4.50(total 2H, each s), 1.60(9H, s), 1.19(6H, s) | 390(M$^+$), 263(100%) |
| 39 | t-Bu | Cl | H | 4-CON(n-Pr)$_2$ | H | H | Viscous oily substance | 7.40(1H, s), 4.57, 4.46(total 2H, each s), 1.60(6H, s), 0.85(6H, t) | 418(M$^+$), 262(100%) |
| 40 | t-Bu | Cl | H | 4-CON⟨ring⟩O | H | H | 85 | 7.41(1H, s), 4.61, 4.51(total 2H, each s), 1.60(9H, s) | 404(M$^+$), 235(100%) |
| 41 | t-Bu | Cl | H | 4-CON⟨ring⟩NMe | H | H | Viscous oily substance | 7.51(1H, s), 4.61, 4.51(total 2H, each s), 2.31(3H, s), 1.60(9H, s) | 417(M$^+$; 100%) |
| 42 | t-Bu | Cl | H | 4-CON⟨ring⟩NEt | H | H | Viscous oily substance | 7.42(1H, s), 4.61, 4.51(total 2H, each s), 1.69(9H, s), 1.59(3H, t) | 431(M$^+$; 100%) |
| 71 | t-Bu | Cl | H | 4-CONH$_2$ | H | H | 256-258 | (CDCl$_3$+DMSO-d$_6$)7.92, 7.40 (each 2H, ABq), 7.48(1H, s), 4.57, 4.47(total 2H, each s), 1.55(9H, s) | |

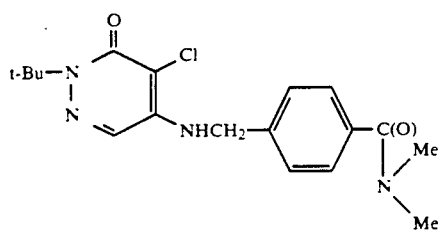

0.65 g of 4,5-dichloro-2-t-butyl-3(2H)pyridazinone, 1.04 g of 4-dimethylaminocarbonylbenzylamine prepared in Reference Example 5, 0.28 g of pyridine, 20 ml of water and 10 ml of 1,4-dioxane were refluxed under stirring for 15 hours. 1,4-dioxane was distilled off under reduced pressure, and the residue was extracted with chloroform. The extract was washed with diluted hydrochloric acid and water, and dried over sodium sulfate, and then the solvent was distilled off. The residue was treated with n-hexane to obtain 480 mg of the above identified compound having a melting point of from 167° to 169° C. as pale yellow crystals.

NMR(CDCl$_3$)δ: 7.43 (1H, ). 7.40 (4H, ), 5.23 (1H, broad s), 4.61, 4.51 (total 2H, each s), 3.04 (6H, s), 1.62 (9H, s).

MS (m/e): 362(M$^+$, 100%).

The compounds as identified in Table 10 were prepared in the synthetic manner and after-treatment similar to those in Example 3 except that the benzylamines

EXAMPLE 4

4-Chloro-5-(4-dimethylaminobenzylamino)-2-t-butyl-3-(2H)pyridazinone hydrochloride (Compound No. 44)

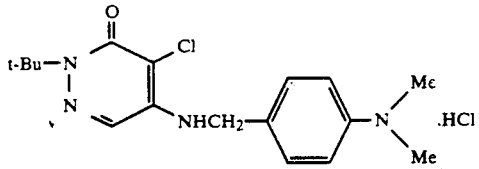

334 ml of 4-chloro-5-(4-dimethylaminobenzylamino)-2-t-butyl-3(2H)pyridazinone (Compound No. 25) prepared in Example 2 was dissolved in a mixed solution of 2 ml of methanol and 2 ml of chloroform. 1.5 ml of a 1,4-dioxane solution of 6N HCl was added to the mixture, and left to stand for 5 minutes while shaking the mixture frequently. The solvent was distilled off under reduced pressure, and the colorless oily substance thereby obtained was dissolved in 15 ml of water and filtrated. The filtrate was subjected to freeze drying, and then to vacuum drying over a solid of sodium hydroxide to obtain 380 mg of the above identified compound as a hygroscopic pale yellow powder.

MS (m/e): 334(M$^+$-HCl, 100%).

In a similar manner as above, the compounds as identified in Table 11 were obtained.

TABLE 11

Synthesis of

[structure shown with R₁—N, N, N—CH₂-phenyl (Y₁, Y₂, Y₃), R₂, R₃, .HCl]

| Compound No. | $R_1$ | $R_2$ | $R_3$ | $Y_1$ | $Y_2, Y_3$ | Properties | MS (m/e) |
|---|---|---|---|---|---|---|---|
| 45 | i-Pr | Cl | H | 4-N(Me)$_2$.HCl | H | Hygroscopic powder | |
| 46 | Et | Cl | H | 4-N(Me)$_2$.HCl | H | Hygroscopic powder | |
| 47 | t-Bu | Br | H | 4-N(Me)$_2$.HCl | H | Hygroscopic powder | |
| 48 | t-Bu | Cl | H | 4-CH$_2$N(Me)$_2$.HCl | H | Hygroscopic powder | 348(M$^+$-HCl; 100%) |
| 49 | t-Bu | Cl | H | 4-CH$_2$N⟨piperazine⟩NEt.2HCl | H | Hygroscopic powder | 417(M$^+$-2HCl; 100%) |
| 50 | t-Bu | Cl | H | 4-CONH(CH$_2$)$_2$N(Me)$_2$.HCl | H | Hygroscopic powder | 370(M$^+$-HCl—Cl) |
| 66 | t-Bu | Cl | Me | 4-NMe$_2$.HCl | H | Hygroscopic powder | 387, 159(100%) |
| 70 | Et | Cl | Me | 4-NMe$_2$.HCl | H | Hygroscopic powder | 302 159 134(100%) |

EXAMPLE 5

4-Chloro-5-(4-methoxycarbonylbenzylamino)-2-t-butyl-3-(2H)pyridazinone (Compound No. 51)

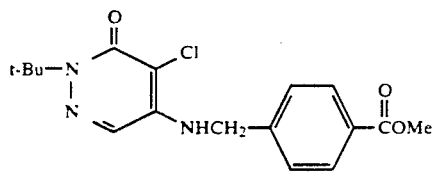

Into a mixture comprising 500 mg of 4-chloro-5-(4-carboxybenzylamino)-2-t-butyl-3(2H)pyridazinone (Compound No. 23) prepared in Example 1, 310 mg of potassium carbonate, 10 ml of acetone and 30 ml of water, 230 mg of dimethyl sulfate was dropwise added under stirring and cooling with ice. After the dropwise addition, the mixture was stirred at the same temperature for 1 hour and at room temperature for further 12 hours. The precipitated crystals were collected by filtration, dissolved in chloroform, washed with an aqueous sodium hydrogencarbonate solution, and dried over sodium salfate, and then, the solvent was distilled off. The residue thereby obtained was crystallized from etherhexane to obtain 60 mg of the above identified compound having a melting point of 153° C. as colorless crystals.

IR ($\nu_{KBrmax}$) cm$^{-1}$: 3310, 1725, 1635 (shoulder), 1605.
NMR(CDCl$_3$)δ: 8.04, 736 (each 2H, ABq) 7.40 (1H, s), 5.45 (1H, broad s), 4.65, 4.55 (total 2H, each s), 3.89 (3H, s), 1.59 (9H, S).
MS (m/e): 349(M$^+$), 149 (100%).

The compounds as identified in Table 12 were prepared in the synthetic manner and after-treatment similar to those in Example 5 except that the carboxylic acids with Y$_1$, Y$_2$, Y$_3$, R$_1$, R$_2$ and R$_3$ as identified in Table 12 were used instead of the starting 4-chloro-5-(4-carboxybenzylamino)-2-t-butyl-3(2H)pyridazinone used in Example 5. For the preparation of Compound No. 52, diethyl sulfate was used as an esterifying agent. In the NMR data, only the characteristic absorptions are given in Table 12.

TABLE 12

Synthesis of

[structure shown with R₁—N, N, NR₃—CH₂-phenyl (Y₁, Y₂, Y₃), R₂]

| Compound No. | $R_1$ | $R_2$ | $R_3$ | $Y_1$ | $Y_2$ | $Y_3$ | mp(°C.) | NMR (CDCl$_3$) δ | MS (m/e) |
|---|---|---|---|---|---|---|---|---|---|
| 52 | t-Bu | Cl | H | 4-CO$_2$Et | H | H | 164–166 | 7.35(1H, s), 4.61, 4.51(total 2H, each s), 1.60(9H, s), 1.38(3H, t) | 363(M$^+$), 163(100%) |

TABLE 12-continued

Synthesis of

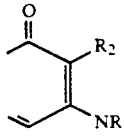

| Compound No. | R₁ | R₂ | R₃ | Y₁ | Y₂ | Y₃ | mp(°C.) | NMR (CDCl₃) δ | MS (m/e) |
|---|---|---|---|---|---|---|---|---|---|
| 53 | t-Bu | Cl | H | 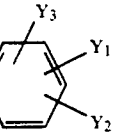 (4-CH=CH-CO₂Me) | H | H | 161–163 | 7.61, 6.36(each 1H, ABq, J=16Hz), 7.36(1H, s), 4.56, 4.46(total 2H, each s), 3.76(3H, s), 1.58(9H, s) | 375(M⁺), 175(100%) |
| 62 | i-Pr | Cl | H | 4-CO₂Me | H | H | 153.5–154.5 | 7.43(1H, s), 4.62, 4.52(total, 2H, each s), 3.87(3H, s), 1.28(6H, d) | 335(M⁺), 149(100%) |

EXAMPLE 6

4-Chloro-5-(4-allylaminocarbonylbenzylamino)-2-t-butyl-3(2H)pyridazinone (Compound No. 54)

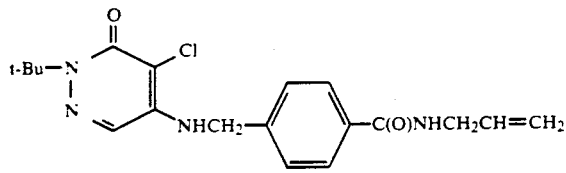

Into a mixture comprising 336 mg of 4-chloro-5-(4-carboxybenzylamino)-2-t-butyl-3(2H)pyridazinone (Compound No. 23) prepared in Example 1 and 5 ml of dimethylformamide, 194 mg of N,N'-carbonyldiimidazole was added under cooling with ice. The mixture was stirred at the same temperature for 1 hour. After the addition of a solution obtained by dissolving 74 mg of allylamine in 2 ml of DMF, the mixture was stirred at the same temperature for 30 minutes, and at room temperature for further 4.5 hours. The solvent was distilled off. The residue thereby obtained was extracted with ethyl acetate. The extract was washed successively with diluted hydrochloric acid, water, a saturated sodium hydrogencarbonate aqueous solution and a saturated sodium chloride aqueous solution, and dried over sodium salfate, and then the solvent was distilled off to obtain a colorless solid substance. This substance was crystallized from ethyl acetate-ether to obtain 210 mg of the above identified compound having a melting point of from 212° to 213.5° C. as colorless crystals.

NMR(CDCl₃+DMSO-d₆)δ: 7.75, 7.25 (each 2H, ABq), 7.32 (1H, s), 4.54, 4.44 (total 2H, each s), 1.56 (9H, s).

MS (m/e): 374(M⁺), 318, 173 (100%), 118.

The compounds as identified in Table 13 were prepared in the synthetic manner and after-treatment similar to those in Example 6 except that the carboxylic acids with R₁, R₂, R₃, Y₁, Y₂ and Y₃ as identified in Table 13 were used instead of the starting 4-chloro-5-(4-carboxybenzylamino)-2-t-butyl-3(2H)pyridazinone used in Example 6, and the amines with Y₁, Y₂ and Y₃ as identified in Table 13 were used instead of the starting allylamine. In the NMR data, only the characteristic absorptions are given in Table 13.

TABLE 13

Synthesis of

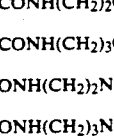

| Compound No. | R₁ | R₂ | R₃ | Y₁ | Y₂ | Y₃ | mp(°C.) | NMR (CDCl₃) δ | MS (m/e) |
|---|---|---|---|---|---|---|---|---|---|
| 55 | t-Bu | Cl | H | 4-CONH(CH₂)₂OMe | H | H | 199.5–200.5 | 7.35(1H, s), 4.60, 4.50(total 2H, each s), 3.34(3H, s), 1.59(9H, s) | 392(M⁺), 262(100%) |
| 56 | t-Bu | Cl | H | 4-CONH(CH₂)₂OEt | H | H | 165 | 7.39(1H, s), 4.62, 4.51(total 2H, each s), 1.61(9H, s), 1.24(3H, s) | 406(M⁺), 262(100%) |
| 57 | t-Bu | Cl | H | 4-CONH(CH₂)₃OEt | H | H | 204 | 7.40(1H, s), 4.61, 4.51(total 2H, each s), 1.60(9H, s), 1.22(3H, t) | 420(M⁺), 335(100%) |
| 58 | t-Bu | Cl | H | 4-CONH(CH₂)₂N(Me)₂ | H | H | 216–218 | 7.35(1H, s), 4.61, 4.51(total 2H, each s), 2.24(6H, s), 1.60(9H, s) | 405(M⁺), 359 |
| 59 | t-Bu | Cl | H | 4-CONH(CH₂)₃N(Me)₂ | H | H | 203 | 7.39(1H, s), 4.60, 4.50(total 2H, each s), 2.36(6H, s), 1.60(9H, s) | 419(M⁺) |
| 60 | t-Bu | Cl | H | 4-CH=CH-CONH-CH₂CH₂-CO₂Et | H | H | 163–166 | 7.38(1H, s), 6.34(1H, d, J=16Hz), 4.55, 4.45(total 2H, each s), 1.59 (9H, s), 1.27(3H, t) | 460(M⁺), 260(100%) |

EXAMPLE 7

4-Ethyl-5-(4-methylbenzylamino)-2-t-butyl-3(2H)pyridazinone (Compound No. 36)

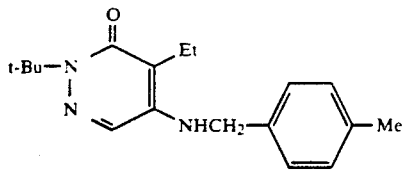

A mixture comprising 260 mg of 4-ethyl-5-chloro-2-t-butyl-3(2H)pyridazinone, 439 mg of 4-methylbenzylamine, 250 mg of potassium carbonate, 4 ml of dimethyl sulfoxide and 0.5 ml of water was stirred at 160° C. for 20 hours. After cooling, 20 ml of 2% diluted hydrochloric acid was poured into the reaction mixture under cooling with ice, and the mixture was extracted with benzene. The extract was washed with water (twice) and a saturated sodium chloride aqueous solution, and dried over sodium sulfate, and then the solvent was distilled off to obtain a pale yellow oily substance. The residue was subjected to silica gel column chromatography, and eluted with benzene-ethyl acetate (4:1, v/v). The pale yellow solid substance thereby obtained was crystallized from n-hexane to obtain 57 mg of pale yellow crystals having a melting point of from 156° to 158° C.

NMR(CDCl$_3$)δ: 7.40 (1H, s), 7.09 (4H, s), 4.35 (2H, s), 2.46 (2H, q), 2.31 (3H, s), 1.59 (9H, s), 1.06 (3H, t).

Mass (m/e): 299(M$^+$), 243 (100%), 105.

The compound as identified in Table 14 was prepared in the synthetic manner and after-treatment similar to those in Example 7 except that the 4-alkyl-5-chloro-2-alkyl-3(2H)pyridazinone with R$_1$ and R$_2$ as identified in Table 14 was used instead of the starting 4-ethyl-5-chloro-2-t-butyl-3(2H)pyridazinone used in Example 7, and the benzylamine derivative with R$_3$, Y$_1$, Y$_2$ and Y$_3$ as identified in Table 14 was used instead of the starting 4-methylbenzylamine. In the NMR data, only the characteristic absorptions were given in Table 14.

EXAMPLE 8

4-Chloro-5-(4-di-n-propylaminomethyl-N-methylbenzylamino)-2-t-butyl-3(2H)pyridazinone (Compound No. 43)

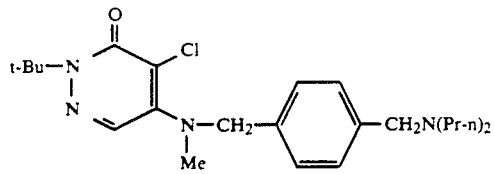

A mixture comprising 0.3 g of 4,5-dichloro-2-t-butyl-3(2H)pyridazinone, 0.65 g of 4-di-n-propylaminomethyl-N-methylbenzylamine prepared in Reference Example 6, 0.19 g of potassium carbonate, 8 ml of 1,4-dioxane and 16 ml of water was stirred under stirring for 8 hours. 1,4-Dioxane was distilled off under reduced pressure, and the residue was extracted with chloroform. Then, the extract was dried over sodium sulfate, and the solvent was distilled off. The residue thereby obtained was purified with silica gel column chromatography by using benzene-ethyl acetate (1:1, v/v) as a developer to obtain 0.15 g of the above identified compound as a viscous oily substance.

NMR(CDCl$_3$)δ: 7.57 (1H, s), 7.28 (4H, s), 4.58 (2H, s), 3.53 (2H, s), 3.01 (3H, s), 2.40 (4H, t), 1.62 (9H, s), 0.86 (3H, t).

MS (m/e): 389(M$^+$-ET, 100%), 382, 317, 262.

The compounds as identified in Table 15 were prepared in the synthetic manner and after-treatment similar to those in Example 8 except that the 4,5-dichloro-2-alkyl-3(2H)pyridazinones with R$_1$ and R$_2$ as identified in Table 15 were used instead of the starting 4,5-dichloro-2-t-butyl-3(2H)pyridazinone used in Example 8, and the N-alkylbenzylamines with R$_3$, Y$_1$, Y$_2$ and Y$_3$ as identified in Table 15 were used instead of the starting 4-di-n-propylaminomethyl-N-methylbenzylamine. In the NMR data, only the characteristic absorptions are given in Table 15.

TABLE 14

Synthesis of

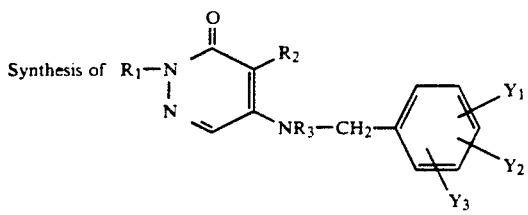

| Compound No. | R$_1$ | R$_2$ | R$_3$ | Y$_1$ | Y$_2$ | Y$_3$ | mp(°C.) | NMR (CDCl$_3$) δ | MS (m/e) |
|---|---|---|---|---|---|---|---|---|---|
| 73 | t-Bu | Me | H | 3-OMe | 4-OMe | H | 182–183.5 | 7.44(1H, s), 4.44, 4.34(total 2H, each s), 3.85(6H, s), 1.95(3H, s), 1.60(9H, s) | 331 (M$^+$), 151(100%) |

TABLE 15

Synthesis of

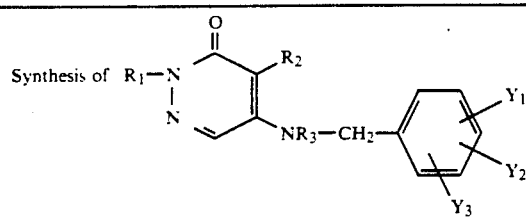

| Compound No. | $R_1$ | $R_2$ | $R_3$ | $Y_1$ | $Y_2$ | $Y_3$ | mp(°C.) | NMR (CDCl₃) δ | MS (m/e) |
|---|---|---|---|---|---|---|---|---|---|
| 65 | t-Bu | Cl | Me | 4-NMe₂ | H | H | Oily substance | 7.55(1H, s), 7.12, 6.66(each 2H, ABq) 4.48 (2H, s) 2.96(3H, s) 2.90(6H, s) 1.62 (9H, s) | 313 159 134(100%) |
| 69 | Et | Cl | Me | 4-NMe₂ | H | H | Oily substance | 7.58(1H, s), 7.08, 6.63(each 2H, ABq) 4.42 (2H, s) 2.92(3H, s) 2.86(9H, s) 1.31 (3H, t) | 285 159 134(100%) |
| 64 | t-Bu | Cl | Me | 4-Me | H | H | 70–71 | 7.51(1H, s) 7.11(4H, s) 4.52(2H, s) 2.98(3H, s) 2.32(3H, s) 1.61(9H, s) | 319(M⁺) 263 105(100%) |
| 67 | Et | Cl | Me | 4-Me | H | H | 74 | 7.53(1H, s) 7.09(4H, s) 4.49(2H, s) 4.10(2H, q) 2.96(3H, s) 2.28(3H, s) 1.28(3H, t) | 291(M⁺) 256 105(100%) |
| 68 | Et | Cl | Me | 3-OMe | H | H | Oily substance | 7.71(1H, s) 4.67(2H, s) 4.26(2H, q) 3.76(3H, s) 3.03(3H, s) 1.34(3H, t) | 307(M⁺) 273(100%) |

EXAMPLE 9

4-Chloro-5-[4-(β-carboxyethylaminocarbonyl-2-transethenyl)benzylamino]-2-t-butyl-3(2H)pyridazinone (Compound No. 61)

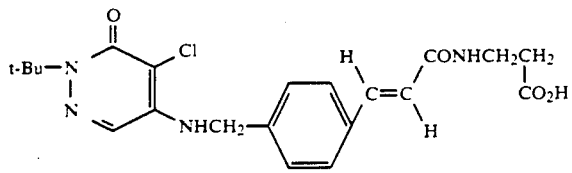

70 mg of the compound prepared in Example 6 (Compound No. 60) was dissolved in 2 ml of MeOH, and 0.2 ml of a 2N sodium hydroxide aqueous solution was added thereto under stirring and cooling with ice, and the mixture was stirred at the same temperature for 1 hour. Diluted hydrochloric acid was added to adjust the pH to a level of about 7, and the reaction mixture was subjected to evaporation under reduced pressure. Diluted hydrochloric acid was poured into the residue thereby obtained, and the mixture was extracted with ethyl acetate. The extract was washed with water (twice) and a saturated sodium chloride aqueous solution, and dried over sodium sulfate, and then the solvent was distilled off to obtain a pale yellow solid substance. This substance was treated with ether to obtain 56 mg of the above identified compound having a melting point of from 170° to 173° C. as colorless crystals.

IR ($\nu^{KBr}_{max}$) cm⁻¹ 3260, 1730, 1650 (shoulder), 1605.
NMR(CDCl₃)δ: 7.55, 6.34 (each 1H, ABq, J=16Hz), 7.40 (1H, s), 4.56, 4.46 (total 2H, each s), 1.59 (9H, s)
MS (m/e): 446(M⁺).

REFERENCE EXAMPLE 1A 3-n-Propoxy-4-methoxybenzylamine hydrochloride

A mixture comprising 38 g of 3-n-propoxy-4-methoxybenzaldehyde, 19.68 g of hydroxylamine sulfate, 10 g of sodium hydroxide, 250 ml of methanol and 200 ml of water, was refluxed under stirring for 30 minutes. After cooling, 20 g of sodium hydroxide was added and dissolved in the mixture, and then 50g of Raney nickel (Ni-Al alloy) was gradually added under cooling with ice. After the completion of the addition, the ice bath was removed, and the mixture was continuously stirred at room temperature for one hour. The reaction mixture was filtered, and methanol in the filtrate was distilled off under reduced pressure, and then the residue thereby obtained was extracted with benzene. The extract was washed with a saturated sodium chloride aqueous solution, and dried over sodium sulfate, and then the solvent was distilled off to obtain a colorless oily substance.

NMR(CDCl₃)δ: 6.6–7.0 (3H, m), 3.93 (2H, t), 3.76 (3H, s), 3.73 (2H, s), 2.08–1.71 (2H, m), 1.50 (2H, s), 1.01 (2H, t).

The residual oily substance was diluted with 200 ml of diethyl ether, and 35 ml of a 1,4-dioxane solution of 6N HCl was added thereto under cooling with ice. The precipitated solid substance was collected by filtration, and washed with ether to obtain 33.65 g of the above identified compound as a colorless powder.

In a similar manner as above, benzylamines having different substituents, i.e. 2,4-dimethyl, 4-ethyl, 3-ethyl-4-methoxy, 3-ethoxy, 2-ethoxy, 4-ethoxy, 3-n-propoxy, 3,5-dimethoxy, 2,3-dimethoxy, 3-ethoxy-4-methoxy, 2,5-dimethoxy, 3-n-propoxy-4-methoxy, 3-methoxy-4-ethoxy, 2-ethoxy-4-methoxy and 3,4,5-trimethoxy, and their hydrochlorides were prepared, respectively, from the corresponding benzaldehydes.

REFERENCE EXAMPLE 2A

3-Benzyloxybenzylamine hydrochloride

A mixture comprising 12.72 g of 3-benzyloxybenzaldehyde, 5.76 g of O-methylhydroxylamine hydrochloride, 9.49 g of pyridine and 130 ml of ethanol was refluxed under stirring for 1.5 hours. The solvent was distilled off under reduced pressure, and water was added to the residue. The mixture was extracted with benzene. The extract was washed with water (twice) and a saturated sodium chloride aqueous solution, and dried over sodium sulfate, and then the solvent was distilled off to obtain O-methylaldoxime as pale yellow crystals.

NMR(CDCl₃)δ: 7.97 (1H, s), 7.33 (5H, s), 7.5-6.8 (4H, m), 5.03 (2H, s), 3.92 (3H, s).

Into a suspension comprising 6.81 g of sodium borohydride and 200 ml of tetrahydrofuran, a solution obtained by dissolving 20.52 g of trifluoroacetic acid in 10 ml of tetrahydrofuran, was dropwise added over a period of 20 minutes under stirring and cooling with ice. After the completion of the dropwise addition, the ice bath was removed, and the reaction solution was stirred at room temperature for one hour, and then a solution obtained by dissolving the above obtained O-methylaldoxime in 50 ml of tetrahydrafuran was added thereto. The reaction was conducted at the same temperature for one hour, and then the mixture was refluxed for two hours. After cooling, ice water was gradually added to the reaction mixture under cooling with ice to decompose the excess reducing agent. Tetrahydrofuran was distilled off, and the residue thereby obtained was extracted with chloroform. The extract was washed with water and a saturated sodium chloride aqueous solution, and dried over sodium sulfate, and then the solvent was distilled off to obtain a colorless semi-solid substance. Then, the residue was dissolved in 250 ml of ether, and 10 ml of a dioxane solution of 6N HCl was gradually added thereto under cooling with ice. The mixture was left to stand still overnight. The precipitated solid substance was collected by filtration, and washed with ether, and then dried to obtain 13.52 g of the above identified compound as a colorless powder. The NMR spectrum of the free amine is as follows:

NMR(CDCl₃)δ: 7.28 (5H, s), 7.3-6.6 (4H, m), 4.96 (2H, s), 3.24 (2H, s), 1.56 (2H, s, disappeared upon the addition of D₂O).

In a similar manner as above, benzylamines having various substituents, i.e. 3-ethyl-4-benzyl, 3-benzyloxy, 4-benzyloxy, 3-ethoxy-4-benzyloxy, 2-benzyloxy-3-ethoxy, 3-n-propoxy-4-benzyloxy, 4-dimethylamino and 4-methylmercapto, and their hydrochlorides, were prepared, respectively, from the corresponding benzaldehydes.

REFERENCE EXAMPLE 3A 4-(1,3-Dioxoranyl)benzylamine

Into a mixture of 3.40 g of sodium borohydride and 200 ml of tetrahydrofuran, a mixed solution of 9.83 g of trifluoroacetic acid and 10 ml of tetrahydrofuran, was dropwise added under stirring and cooling with ice. The ice bath was removed, and the reaction mixture was stirred at room temperature for one hour. Then, 30 ml of a tetrahydrofuran solution containing 13.13 g of 4-cyanobenzaldehyde ethylene acetal, was added to the reaction mixture, and the mixture was stirred at room temperature for 4.5 hours. Ice pieces were added thereto on the ice bath to decompose the excess reducing agent, and the solvent was distilled off under reduced pressure. The residue thereby obtained was extracted with chloroform. The extract was washed with water and a saturated sodium chloride aqueous solution, and dried over sodium sulfate, and then the solvent was distilled off to obtain 11.95 g of the above identified compound as a pale yellow semi-solid substance.

NMR(CDCl₃)δ: 5.72 (1H, s), 4.00 (4H, s), 2.30 (2H, broad s, disappeared upon the addition of D₂O).

REFERENCE EXAMPLE 4A

4-Methyl-5-chloro-3(2H)pyridazinone

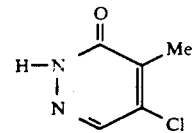

Into a 500 ml flask, 189 g of methylmagnesium bromide (1 mol/liter of an ether solution) was charged, and 10.0 g of 4,5-dichloro-3(2H)pyridazinone was gradually added thereto at a temperature of about 15° C. The mixture was stirred at a temperature of from 40° to 50° C. for about 3 hours. The disappearance of the starting dichloropyridazinone was confirmed by thin layer chromatography (developer; ethyl acetate:acetone = 2:1, v/v), whereupon the reaction was terminated. The reaction solution was transferred to a separating funnel, and about 300 ml of a saturated sodium chloride aqueous solution was added thereto, and then the mixture was vigorously shaken. The aqueous layer was removed. The organic layer was washed with about 200 ml of water, and dried over anhydrous sodium sulfate, and then the solvent was distilled off. The brown crystals thereby obtained were recrystallized from ethyl acetate to obtain 4.54 g of the above identified compound having a melting point of from 132° to 134° C. as colorless crystals.

NMR(CDCl₃) δ: 2.27 (3H, s), 7.72 (1H, s), 12.52 (1H, broad s).

MS (m/e): 143(M+).

REFERENCE EXAMPLE 5A

4-Methyl-5-chloro-2-i-propyl-3(2H)pyridazinone

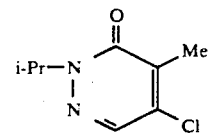

Into a 200 ml four-necked flask, 4.54 g (0.032 mol) of 4-methyl-5-chloro-3(2H)pyridazinone prepared in Reference Example 4A, 6.34 g (0.038 mol) of isopropyl iodide and 60 ml of dimethylformamide were charged, and 1.66 g of sodium hydride (50% mineral oil suspension) was gradually added thereto at a temperature of about 5° C. The mixture was stirred at 30° C. for about 3 hours.

The disappearance of the starting material was confirmed by thin layer chromatography (developer; chloroform), whereupon the reaction was terminated. 60 ml of benzene and 100 ml of a 10% hydrochloric acid aqueous solution were added thereto, and the mixture was vigorously shaken. The aqueous layer was removed. The organic layer was washed once with 50 ml of a saturated sodium chloride aqueous solution, and dried over anhydrous sodium salfate, and then the solvent was distilled off. The oily substance thereby obtained was separated and purified by silica gel column chromatography (developer; benzene:chloroform = 1:1 v/v) to obtain 2.85 g of the above identified compound.

Melting point: 40° C.

NMR(CDCl₃)δ: 7.76 (1H, s), 5.26 (1H, m), 2.27 (3H, s) 1.40 (3H, s), 1.29 (3H, s).

EXAMPLE 1A

4-Chloro-5-(3-benzyloxybenzylamino)-2-i-propyl-3-(2H)pyridazinone (Compound No. 95)

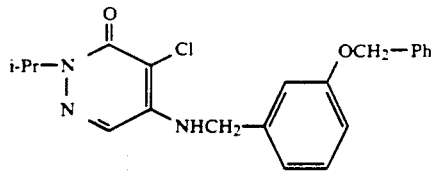

A mixture comprising 8.24 g of 3-benzyloxybenzylamine hydrochloride prepared in Reference Example 2A, 3.11 g of 2-i-propyl-4,5-dichloro-3(2H)pyridazinone, 7.26 g of potassium carbonate, 30 ml of 1,4-dioxane and 90 ml of water was refluxed under stirring for 4.5 hours. The majority of 1,4-dioxane was distilled off under reduced pressure, and the residue was extracted with ethyl acetate. The extract was washed with diluted hydrochloric acid, and then treated with cerite to remove the precipitate. The organic layer was separated, and washed with water and a saturated sodium chloride aqueous solution, and then dried over sodium sulfate. Then, the solvent was distilled off. The pale yellow oily substance thereby obtained was crystallized from ether-n-hexane to obtain 2.51 g of the above identified compound having a melting point of from 106° to 108° C. as colorless crystals.

NMR(CDCl$_3$)δ: 7.48 (1H, s), 7.30 (5H, s), 7.3–6.7 (4H, m), 5.02 (2H, s), 4.49, 4.40 (total 2H, each s), 5.2–4.8 (1H, broad s), 1.30 (6H, d).

MS (m/e): 383(M$^+$), 348, 91 (100%).

EXAMPLE 2A

4-Chloro-5-(3-n-propoxy-4-methoxybenzylamino)-2-i-propyl-3(2H)pyridazinone (Compound No. 106)

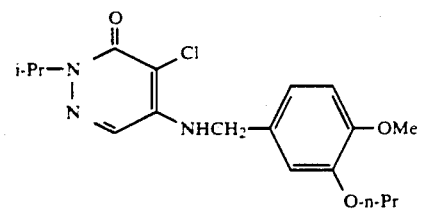

A mixture comprising 1.34 g of 3-n-propoxy-4-methoxybenzylamine hydrochloride, 0.4 g of 4,5-dichloro-2-i-propyl-3(2H)pyridazinone, 1.08 g of potassium carbonate, 6 ml of 1,4-dioxane and 18 ml of water was refluxed under stirring for 8 hours. The solvent was distilled off under reduced pressure, and water was added to the the residue thereby obtained, and then the mixture was extracted with ethyl acetate. The extract was washed successively with diluted hydrochloric acid, water and a saturated sodium chloride aqueous solution, and dried over sodium sulfate, and then the solvent was distilled off. The product was crystallized from ethyl acetate-diethyl ether-n-hexane to obtain 230 mg of the above identified compound having a melting point of from 120° to 122° as colorless crystals.

NMR(CDCl$_3$)δ: 7.58 (1H, s), 6.81 (3H, s), 5.38–4.93 (2H, m), 4.47, 4.37 (total 2H, each s), 3.94 (2H, t), 3.83 (3H, s), 2.05–1.65 (2H, m) 1.28 (6H, d), 1.02 (3H, t)

MS (m/e): 365(M$^+$), 330, 179 (100%), 137.

EXAMPLE 3A

4-Chloro-5-(4-di-n-propylaminocarbonylbenzylamino)-2-i-propyl-3(2H)pyridazinone (Compound No. 125)

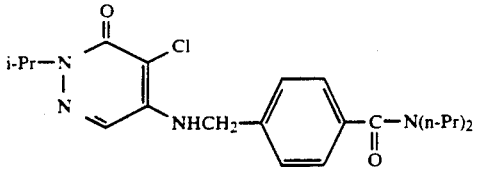

A mixture of 322 mg of 4-chloro-5-(4-carboxy-benzylamino)-2-i-propyl-3(2H)pyridazinone obtained from 2-i-propyl-4,5-dichloro-3(2H)pyrisazinone and 4-carbonxybenzylamine, 194 mg of N,N'-carbonyldiimidazole and 5 ml of dimethylformamide, was stirred at room temperature for one hour. A solution obtained by dissolving 100 mg of di-n-propylamine in 1 ml of dimethylformamide was added thereto, and the mixture was stirred at the same temperature overnight. The solvent was distilled off under reduced pressure, and the pale yellow oily substance thereby obtained was extracted with chloroform. The extract was washed successively with diluted hydrochloric acid, water, a 5% sodium hydroxide aqueous solution and a saturated sodium chloride aqueous solution, and dried over sodium sulfate, and then the solvent was distilled off to obtain a pale yellow oily substance. This substance was subjected to silica gel column chromatography and eluted with benzene:ethyl acetate (2:5, v/v). The colorless viscous oily substance thereby obtained was crystallized from ether-n-hexane to obtain 108 mg of the above identified compound having a melting point of from 78° to 81° C. as colorless crystals.

NMR(CDCl$_3$)δ: 7.48 (1H, s), 7.28 (4H, s), 4.58, 4.48 (total 2H, each s), 3.7–2.9 (4H, m), 1.8–0.5 (10H, m), 1.29 (6H, d).

MS (m/e): 404(M$^+$), 304 (100%), 217, 100.

EXAMPLE 4A

4-Chloro-5-(3-hydroxybenzylamino)-2-i-propyl-3-(2H)pyridazinone (Compound No. 137)

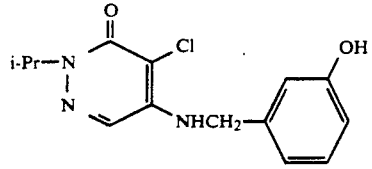

Into a mixture comprising 1.15 g of 4-chloro-5-(3-benzyloxybenzylamino)-2-i-propyl-3(2H)pyridazinone (Compound No. 95) prepared in Example 1A, 10 ml of dimethyl sulfide and 4 ml of dichloromethane, 3.41 g of boron trifluoride etherate was added under cooling with ice. The mixture was stirred at 0° C. for 30 minutes and at room temperature for further 24 hours. The reaction solution was cooled with ice and 40 ml of n-hexane was added thereto, whereby a pale yellow solid substance was precipitated. The solid substance was collected by filtration, and washed with n-hexane, and then treated with ethyl acetate and water. The organic layer was separated, and washed with water and a saturated sodium chloride aqueous solution, and dried over sodium sulfate, and then the solvent was distilled off to obtain a pale yellow solid substance. This substance was crystallized from ethyl acetate-ether to obtain 730 mg of the above identified compound having a melting point of from 194.5 to 196° C. as colorless crystals.

NMR(CDCl₃+DMSO-d₆)κ: 7.51 (1H, s), 6.6–7.2(4H, m), 6.3–5.8 (1H, broad s), 4.5, 4.4 (total 2H, each s), 1.26 (6H, d).

MS (m/e): 293(M⁺), 258, 251, 216 (100%), 107.

EXAMPLE 5A

4-Chloro-5-[3-(4-t-butoxycarbonyl)butoxybenzylamino]-2-i-propyl-3(2H)pyridazinone (Compound No. 139)

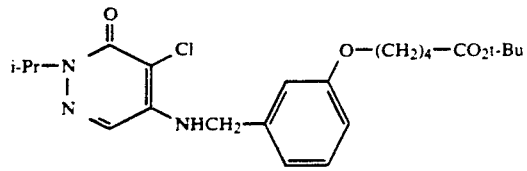

A mixture comprising 2.056 g of 4-chloro-5-(3-hydroxybenzylamino)-2-i-propyl-3(2H)pyridazinone (Compound No. 137) prepared in Example 4A, 5.807 g of t-butyl 5-bromovalerate, 2.62 g of sodium iodide, 4.64 g of potassium carbonate and 50 ml of methyl ethyl ketone, was refluxed under stirring for 3 days. Water was poured into the reaction mixture, and the mixture was extracted with ethyl acetate. The extract was washed with water and a saturated sodium chloride aqueous solution, and dried over sodium sulfate, and then the solvent was distilled off to obtain a pale violety red oily substance. This product was subjected to silica gel column chromatography, and the fraction eluted with benzene-ethyl acetate (3:1, v/v) was subjected to distillation to obtain 3.21 g of the above identified compound as a pale yellow viscous oily substance.

NMR(CDCl₃)δ: 7.55 (1H, s), 7.4–6.7 (4H, m), 4.63, 4.52 (total 2H, each s), 1.43 (9H, s), 1.30 (6H, s).

MS (FD; m/e): 449(M⁻).

EXAMPLE 6A

4-Chloro-5-[3-(4-carboxy)butoxybenzylamino]-2-i-propyl-3(2H)pyridazinone (Compound No. 142)

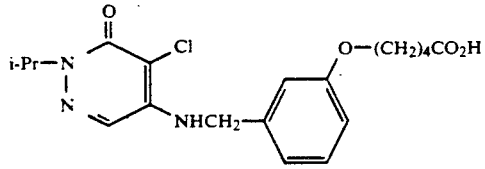

In 30 ml of a 1,4-dioxane solution of 6N HCl, 3.00 g of 4-chloro-5-[3-(4-t-butoxycarbonyl)butoxybenzylamino]-2-i-propyl-3(2H)pyridazinone (Compound No. 139) prepared in Example 5A was dissolved, and the mixture was stirred at room temperature for 50 minutes. The solvent was distilled off under reduced pressure. The dark yellowish orange oily substance thereby obtained was subjected to silica gel column chromatography, and eluted with chlroform-methanol (24:1, v/v) to obtain 1.75 g of the above identified compound as a colorless foamed substance.

NMR(CDCl₃)δ: 7.51 (1H, s), 7.4–6.9 (1H, broad s, disappeared upon the addition of D₂O), 7.2–6.6 (4H, m), 4.50, 4.40 (total 2H, each s), 3.95 (2H, collapsed t), 2.42 (2H, collapsed t), 2.0–1.6 (4H, m), 1.30 (6H, d).

MS (FD; m/e): 394(M++1).

EXAMPLE 7A

4-Chloro-5-[3(4-methoxycarbonyl)butoxybenzylamino-2-i-propyl-3(2H)pyridazinone (Compound No. 144)

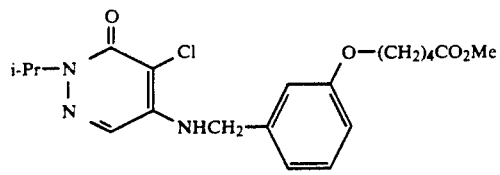

Into 30 ml of an ethyl acetate solution containing 1.30 g of 4-chloro-5-[3-(4-carboxy)butoxybenzylamino]-2-i-propyl-3(2H)pyridazinone (Compound No. 142) prepared in Example 6A, diazomethane was bubbled until the solution was colored pale yellow, and the reaction solution was left to stand still overnight. The solvent was distilled off to obtain 1.35 g of the above identified compound as a pale yellow oily substance.

NMR(CDCl₃)δ: 7.51 (1H, s), 7.2–6.6 (4H, m), 4.51, 4.41 (total 2H, each s), 3.92 (2H, collapsed t), 3.62 (3H, s), 2.38 (2H, collapsed t), 2.0–1.5 (4H, m), 1.28 (6H, d).

MS (FD; m/e): 407(M⁺).

EXAMPLE 8A

4-Chloro-5-[3-(4-N-methylaminocarbonyl)butoxybenzylamino]-2-i-propyl-3(2H)pyridazinone (Compound No. 146)

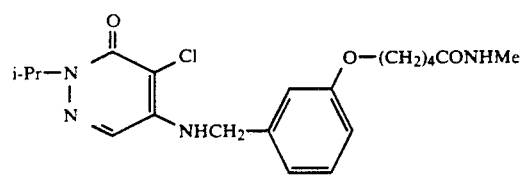

A mixture comprising 280 mg of 4-chloro-5-[3-(4-methoxycarbonyl)butoxybenzylamino)-2-i-propyl-3(2H)-pyridazinone (Compound No. 144) prepared in Example 7A, 2.0 ml of methylamine (40% aqueous solution) and 2.0 ml of methanol, was stirred at room temperature for 2 days. The reaction solution was distilled off under reduced pressure, and the residue thereby obtained was extracted with ethyl acetate. The extract was washed with water and a saturated sodium chloride aqueous solution, and dried over sodium sulfate, and then the solvent was distilled off to obtain 280 mg of the above identified compound as a pale yellow viscous oily substance.

NMR(CDCl₃)δ: 7.51 (1H, s), 4.53, 4.43 (total 2H, each s), 3.91 (2H, collapsed t), 2.74 (3H, d), 2.5–1.6 (6H, m), 1.28 (6H, d).

MS (FD; m/e): 406(M⁺).

EXAMPLE 9A

4-Chloro-5-[3-(5-hydroxy)pentoxybenzylamino]-2-i-propyl-3(2H)pyridazinone (Compound No. 147)

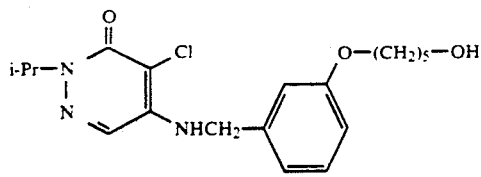

Into 30 ml of a toluene solution containing 1.02 g of 4-chloro-5-[3-(4-methoxycarbonyl)butoxybenzylamino]-2-i-propyl-3(2H)pyridazinone (Compound No. 144) prepared in Example 7A on the ice bath, 2.0 ml of a toluene solution containing 70% of sodium bismethoxyethoxyaluminum hydride was dropwise added, and the mixture was stirred for 1 hour. Diluted hydrochloric acid was gradually added to the reaction solution to decompose the excess reducing agent, and the mixture was extracted with chloroform. The extract was washed with water and a saturated sodium chloride aqueous solution, and dried over sodium salfate, and then the solvent was distilled off to obtain a dark violety red oily substance. This substance was purified by silica gel column chromatography eluting with chloroform-methanol (25:1, v/v) to obtain 587 mg of the above identified compound as a pale yellow viscous oily substance.

NMR(CDCl$_3$ +D$_2$O)δ: 7.50 (1H, s), 7.3-6.6 (4H, m), 4.51, 4.42 (total 2H, each s), 3.94 (2H, collapsed t), 3.64 (2H, collapsed t), 2.0-1.4 (6H, m), 1.29 (6H, d).

MS (FD; m/e): 379(M⁻).

EXAMPLE 10A

4-Chloro-5-[3-(5-methoxy)pentoxy-N-methylbenzylamino]-2-i-propyl-3(2H)pyridazinone (Compound No. 149)

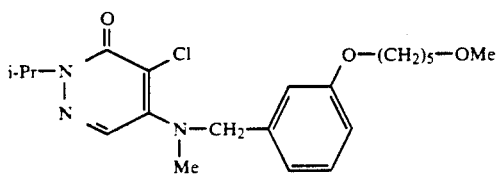

Into 10 ml of a tetrahydrofuran solution containing 420 mg of 4-chloro-5-[3-(5-hydroxy)pentoxybenzylamino]-2-i-propyl-3(2H)pyridazinone (Compound No. 147) prepared in Example 9A, 121 mg of sodium hydride (55% mineral oil-dispersed powder) was gradually added under cooling with ice, and the mixture was stirred for 10 minutes. 0.2 ml of methyl iodide was added thereto, and the mixture was stirred at the same temperature for 50 minutes. A 10% ammonium chloride aqueous solution was added to the reaction solution, and the mixture was extracted with ethyl acetate. The extract was washed with water and a saturated sodium chloride aqueous solution, and dried over sodium sulfate, and the solvent was distilled off to obtain a pale yellow viscous oily substance. The substance was purified by silica gel column chromatography, whereby 40 mg of the above identified compound was obtained as a pale yellow viscous oily substance from the fraction initially eluted with benzene-ethyl acetate (1:1, v/v).

NMR(CDCl$_3$)δ: 7.51 (1H, s), 7.3-6.6 (4H, m), 4.54 (2H, =), 3.92 (2H, collapsed t), 3.38 (2H, collapsed t), 3.29, 3.01 (each 3H, s), 2.0-1.4 (6H, m), 1.32 (6H, d).

MS (FD; m/e): 407(M⁺).

EXAMPLE 11A

4-Chloro-5-[3-(5-hydroxy)pentoxy-N-methyl-benzylamino]-2-i-propyl-3(2H)pyridazinone (Compound No. 150)

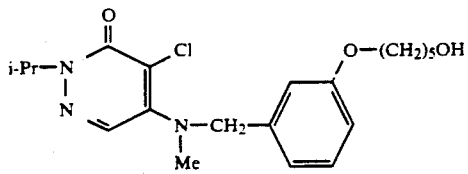

In the silica gel column chromatography operation in Example 10A, 403 mg of the above identified compound was obtained as a colorless viscous oily substance from the second fraction eluted with benzene-ethyl acetate (1:1, (v/v).

NMR(CDC13 +D$_2$O)δ: 7.59 (1H, s), 7.3-6.6 (4H, m), 4.52 (2H, s), 3.92 (2H, collapsed t), 3.62 (2H, collapsed t), 3.01 (3H, s), 2.0-1.4 (6H, m), 1.30 (6H, d).

MS (FD; m/e): 393(M⁺).

EXAMPLE 12A

4-Methyl-5-(4-methoxybenzylamino)-2-i-propyl-3(2H)-pyridazinone (Compound No. 151)

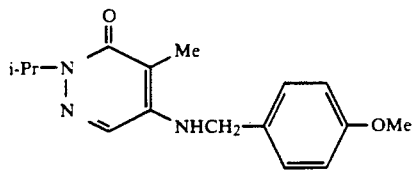

A mixture comprising 2.2 g of 4-methoxybenzylamine, 0.30 g of 4-methyl-5-chloro-2-i-propyl-3(2H)pyridazinone, 1.34 g of sodium hydrogencarbonate, 0.23 g of potassium carbonate and 5 ml of tri-n-propylamine, was heated at 150° C. for 18 hours. The reaction mixture was acidified with a 10% hydrochloric acid aqueous solution, and extracted with 60 ml of benzene. The benzene layer was washed with water, and dried over anhydrous sodium sulfate, and then the solvent was distilled off to obtain an oily substance. This substance was crystallized from 5 ml of ethyl ether to obtain 40 mg of the above identified compound.

Melting point: 172°-174° C.

NMR(CDCl$_3$)δ: 7.55 (1H, s), 4.41, 4.33 (total 2H, each s), 3.78 (3H, s), 1.98 (3H, s), 1.28 (6H, d).

MS (m/e): 287(M⁺), 121 (100%).

EXAMPLE 13A 5-(2,4-dimethoxybenzylamino)-2-i-propyl-3(2H)pyridazinone (Compound No. 100)

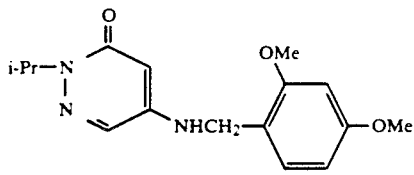

320 mg of 4-chloro-5-(2,4-dimethoxybenzylamino)-2-i-propyl-3(2H)pyridazinone (Compound No. 97), 50 ml of ethanol, 1 ml of triethylamine and 100 mg of palladium-carbon were stirred, and hydrogen was added to the mixture at a temperature of from 40° to 50° C. for 3 hours. The reaction mixture was filtered, and the filtrate was evaporated. The crude crystals thereby obtained were recrystallized from ethyl ether to obtain 230 mg of the above identified compound having a melting point of from 167 to 168° C.

NMR(CDCl$_3$)δ: 7.33 (1H, dd), 5.70 (1H, dd), 5.20 (1H, t), 4.80 (1H, broad), 4.20, 4.10 (total 2H, each s), 3.79 (3H, s), 3.75 (3H, s), 1.26 (6H, d)

MS (m/e): 305(M$^-$), 151 (100%).

EXAMPLE 14A

4-Chloro-5-(4-formylbenzylamino)-2-i-proyl-3(2H)pyridazinone (Compound No. 140)

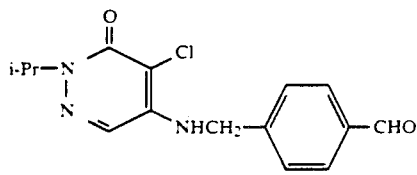

A mixture comprising 11.95 g of 4-(1,3-dioxoranyl)-benzylamine prepared in Reference Example 3A, 5.18 g of 2-i-propyl-4,5-dichloro-3(2H)pyridazinone, 4.15 g of potassium carbonate, 120 ml of water and 40 ml of 1,4-dioxane, was refluxed under stirring for 8 hours. The majority of 1,4-dioxane was distilled off under reduced pressure, and then the residue was extracted with ethyl acetate. The extract was washed with water and a saturated sodium chloride aqueous solution, and dried over sodium sulfate, and the solvent was distilled off to obtain a pale yellow oily substance. This oily residue was dissoved in a mixed solution of 100 ml of tetrahydrofuran and 2 ml of water, and 4 ml of a dioxane solution of 6N HCl was added thereto. The mixture was stirred at room temperature for 1.5 hours. The solvent was distilled off under reduced pressure, and diluted hydrochloric acid was poured into the residue, and then the mixture was extracted with ethyl acetate. The extract was washed with water and a saturated sodium chloride aqueous solution, and dried over sodium sulfate, and then the solvent was distilled off to obtain a pale yellow oily substance. The substance was crystallized from ethyl acetate-ether-n-hexane to obtain 2.01 g of the above identified compound having a melting point of from 93.5° to 95° C. as colorless crystals. The mother liquid for crystallization was concentrated, and subjected to silica gel column chromatography eluted with benzene-ethyl acetate (1:1, v/v) to further obtain 1.09 g (total yield: 3.10 g) of the above identified compound.

NMR(CDCl$_3$)δ: 9.95 (1H, s), 7.85, 7.44 (4H, ABq) 7.45 (1H, s), 4.68, 4.58 (total 2H, each s) 1 28 (6H, d).

MS (m/e): 305(M$^-$), 263 (100%), 119.

EXAMPLE 15A

4-Bromo-5-(4-ethoxybenzylamino)-2-i-propyl-3(2H)pyridazinone (Compound No. 164)

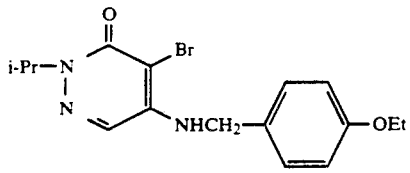

A mixture of 0.38 g of 4-ethoxybenzylamine hydrochloride, 0.4 g of 4,5-dibromo-2-iso-propyl-3(2H)pyridazinone, 0.34 g of potassium carbonate, 6 ml of 1,4-dioxane and 18 ml of water, was heated at 90° C. under stirring for 10 hours. The sovent was distilled off under reduced pressure, and water was added to the residue thereby obtained, and the mixture was extracted with ethyl acetate. The extract was washed with diluted hydrochloric acid and a saturated sodium chloride aqueous solution, and dried over sodium sulfate, and then the solvent was distilled off. The product was crystallized from ether to obtain 220 mg of the above identified compound having a melting point of from 151° to 152.5° C. as pale yellow crystals.

NMR(CDCl$_3$)δ: 7.68 (1H, s), 7.30, 6.96 (4H, ABq) 4.95–5.60 (2H, m), 4.58, 4.48 (total 2H, each s), 4.10 (2H, q), 1.50 (3H, t), 1.40 (6H, d).

MS (m/e): 365(M$^-$) 286 244, 135 (100%).

EXAMPLE 16A

4-Chloro-5-(benzylamino)-2-i-propyl-3(2H)pyridazinone (Compound No. 74)

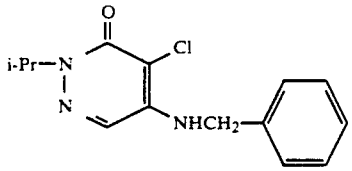

In 6 ml of dry dimethylformamide, 1.875 g of 4-chloro-5-amino-2-i-propyl-3(2H)pyridazinone was dissolved. 0.48 g of sodium hydride (50% mineral oil suspension) was added thereto at a temperature of from 5° to 10° C., and the mixture was stirred for about 30 minutes. Then, 1.4 g of benzyl chloride was dropwise added thereto at the same temperature. After the dropwise addition, the mixture was stirred at room temperature for 2 hours. To the reaction solution, 50 ml of benzene and 30 ml of a 10% hydrochloric acid aqueous solution were added, and the mixture was vigorously shaken. The organic layer was washed with water, and dried, and then the solvent was distilled off. The crude crystals thereby obtained were recrystallized from ethyl ether to obtain 2.3 g of the above identified compound having a melting point of from 131° to 132° C.

NMR(CDCl$_3$)δ: 7.45 (1H, s), 5.08 (1H, broad s), 4.55, 4.46 (total 2H, each s), 1.26 (6H, d).

MS (m/e): 277(M$^+$), 235 (100%).

The compounds prepared in accordance with the above Examples are shown in Table 1A. In the right hand end column in the Table, the numbers of the Examples in accordance with which the respective compounds were prepared, are indicated.

TABLE 1A

Synthesis of

[Structure shown with R1-N-N ring bearing R2, C=O, and N(R3)-CH2-phenyl with Y1, Y2, Y3 substituents]

| Compound No. | R₁ | R₂ | R₃ | Y₁ | Y₂ | Y₃ | mp(°C.) | MS (m/e) | Example No. |
|---|---|---|---|---|---|---|---|---|---|
| 74 | i-Pr | Cl | H | H | H | H | 131–132 | see Example 16A | 16A |
| 75 | Et | Cl | H | 3-Me | H | H | 131–132 | 277 (M⁺), 105 (100%) | 2A |
| 76 | i-Pr | Cl | H | 3-Me | H | H | 149–149.5 | 291 (M⁺), 105 (100%) | 2A |
| 77 | i-Pr | Cl | H | 4-Me | H | H | 176 | 291 (M⁺), 105 (100%) | 2A |
| 78 | i-Pr | Cl | H | 2-Me | H | H | 146 | 291 (M⁺), 105 (100%) | 2A |
| 79 | Et | Cl | H | 2-Me | 4-Me | H | 135–137 | 291 (M⁺), 119 (100%) | 2A |
| 80 | i-Pr | Cl | H | 2-Me | 4-Me | H | 176–177 | 305 (M⁺), 119 (100%) | 2A |
| 81 | Et | Cl | H | 4-Et | H | H | 127 | 291 (M⁺), 119 (100%) | 2A |
| 82 | i-Pr | Cl | H | 3-Et | 4-OCH₂Ph | H | 120–121 | 411 (M⁺), 91 (100%) | 1A |
| 83 | Et | Cl | H | 3-Et | 4-OCH₂Ph | H | 144–145 | 397 (M⁺), 91 (100%) | 1A |
| 84 | i-Pr | Cl | H | 3-Et | 4-OMe | H | 152–153 | 335 (M⁺), 149 (100%) | 2A |
| 85 | Et | Cl | H | 3-Et | 4-OMe | H | 141–142 | 321 (M⁺), 149 (100%) | 2A |
| 86 | i-Pr | Cl | H | 2-OMe | H | H | 148–149.5 | 307 (M⁺), 265 (100%) | 2A |
| 87 | i-Pr | Cl | H | 4-OMe | H | H | 142 | 307 (M⁺), 121 (100%) | 2A |
| 88 | Et | Cl | H | 3-OEt | H | H | 131 | 307 (M⁺), 272 (100%) | 2A |
| 89 | i-Pr | Cl | H | 3-OEt | H | H | 136.5 | 321 (M⁺), 135 (100%) | 2A |
| 90 | Et | Cl | H | 2-OEt | H | H | 120–122 | 307 (M⁺), 135 (100%) | 2A |
| 91 | i-Pr | Cl | H | 4-OEt | H | H | 128–129 | 321 (M⁺), 135 (100%) | 2A |
| 92 | i-Pr | Cl | H | 2-OEt | H | H | 99 | 321 (M⁺), 135 (100%) | 2A |
| 93 | Et | Cl | H | 3-O-n-Pr | H | H | 96 | 321 (M⁺), 286 (100%) | 2A |
| 94 | i-Pr | Cl | H | 3-O-n-Pr | H | H | 119 | 335 (M⁺), 300 (100%) | 2A |
| 95 | i-Pr | Cl | H | 3-OCH₂Ph | H | H | 106–108 | see Example 1A | 1A |
| 96 | i-Pr | Cl | H | 4-OCH₂Ph | H | H | 140.5–141.5 | 383 (M⁺), 91 (100%) | 1A |
| 97 | i-Pr | Cl | H | 2-OMe | 4-OMe | H | 125–126 | 337 (M⁺), 151 (100%) | 2A |
| 98 | i-Pr | Cl | H | 3-OMe | 5-OMe | H | 139 | 337 (M⁺), 302 (100%) | 2A |
| 99 | Et | Cl | H | 2-OMe | 4-OMe | H | 110–111.5 | 323 (M⁺), 151 (100%) | 2A |
| 100 | i-Pr | H | H | 2-OMe | 4-OMe | H | 167–168 | see Example 13A | 13A |
| 101 | i-Pr | Cl | H | 2-OMe | 3-OMe | H | 121–123 | 303 (M⁺), 151 (100%) | 2A |
| 102 | Et | Cl | H | 3-OEt | 4-OMe | H | 134 | 337 (M⁺), 165 (100%) | 2A |
| 103 | i-Pr | Cl | H | 3-OEt | 4-OMe | H | 112–113 | 351 (M⁺), 165 (100%) | 2A |
| 104 | i-Pr | Cl | H | 2-OMe | 5-OMe | H | 123–124 | 337 (M⁺), 151 (100%) | 2A |
| 105 | Et | Cl | H | 3-O-n-Pr | 4-OMe | H | 106.5–107.5 | 351 (M⁺), 179 (100%) | 2A |
| 106 | i-Pr | Cl | H | 3-O-n-Pr | 4-OMe | H | 120–122 | see Example 2A | 2A |
| 107 | i-Pr | Cl | H | 3-OMe | 4-OEt | H | 125 | 351 (M⁺), 165 (100%) | 2A |
| 108 | Et | Cl | H | 3-OMe | 4-O-n-Pr | H | 112–113 | 351 (M⁺), 137 (100%) | 2A |
| 109 | i-Pr | Cl | H | 2-OEt | 4-OMe | H | 113 | 351 (M⁺), 165 (100%) | 2A |
| 110 | Et | Cl | H | 2-OMe | 3-OEt | H | 100–101.5 | 337 (M⁺), 165 (100%) | 2A |
| 111 | i-Pr | Cl | H | 2-OMe | 3-OEt | H | 136–137 | 351 (M⁺), 165 (100%) | 2A |
| 112 | Et | Cl | H | 2-O-n-Pr | 4-OMe | H | Oil | 351 (M⁺), 179 (100%) | 2A |
| 113 | i-Pr | Cl | H | 3-OEt | 4-OCH₂Ph | H | 112–113.5 | 427 (M⁺), 91 (100%) | 1A |
| 114 | i-Pr | Cl | H | 2-OCH₂Ph | 3-OEt | H | 143–144 | 427 (M⁺), 91 (100%) | 1A |
| 115 | Et | Cl | H | 3-OEt | 4-OCH₂Ph | H | 127–128 | 413 (M⁺), 91 (100%) | 1A |
| 116 | Et | Cl | H | 2-OCH₂Ph | 3-OEt | H | 90 | 413 (M⁺), 91 (100%) | 1A |
| 117 | i-Pr | Cl | H | 3-O-n-Pr | 4-OCH₂Ph | H | 104–104.5 | 441 (M⁺), 91 (100%) | 1A |
| 118 | Et | Cl | H | 3-O-n-Pr | 4-OCH₂Ph | H | 145.5–146 | 427 (M⁺), 91 (100%) | 1A |
| 119 | i-Pr | Cl | H | 3-O-CH₂-O-4 | | H | 149.5–150.5 | 321 (M⁺), 135 (100%) | 2A |
| 120 | t-Bu | Cl | H | 3-OMe | 4-OMe | 5-OMe | 166 | 381 (M⁺), 181 (100%) | 2A |
| 121 | Et | Cl | H | 3-OMe | 4-OMe | 5-OMe | 170–172 | 353 (M⁺), 181 (100%) | 2A |
| 122 | i-Pr | Cl | H | 3-OMe | 4-OMe | 5-OMe | 177 | 367 (M⁺), 181 (100%) | 2A |
| 123 | i-Pr | Cl | H | 4-Cl | H | H | 152–152.5 | 311 (M⁺), 125 (100%) | 2A |
| 124 | Et | Cl | H | 4-SMe | H | H | 136–137 | 309 (M⁺), 137 (100%) | 2A |
| 125 | i-Pr | Cl | H | 4-CON(n-Pr)₂ | H | H | 78–81 | see Example 3A | 3A |

TABLE 1A-continued

Synthesis of $$\text{structure with } R_1\text{-N, N, R_2, R_3, Y_1, Y_2, Y_3}$$

| Compound No. | $R_1$ | $R_2$ | $R_3$ | $Y_1$ | $Y_2$ | $Y_3$ | mp(°C.) | MS (m/e) | Example No. |
|---|---|---|---|---|---|---|---|---|---|
| 126 | n-Pr | Cl | H | 4-N(Me)(Me) | H | H | 127-128 | 320 (M+), 134 (100%) | 2A |
| 127 | i-Pr | Cl | H | 2-OH | 3-OEt | H | 159-160 | 337 (M+), 145 (100%) | 4A |
| 128 | i-Pr | H | H | 2-OH | 3-OEt | H | 214.5-215.5 | 303 (M+), 111 (100%) | 4A |
| 129 | Et | Cl | H | 2-OH | 3-OEt | H | 179-180 | 323 (M+), 145 (100%) | 4A |
| 130 | i-Pr | Cl | H | 4-OH | H | H | 165-166 | 293 (M+), 145 (100%) | 4A |
| 131 | i-Pr | Cl | H | 3-Et | 4-OH | H | 201-203 | 321 (M+), 134 (100%) | 4A |
| 132 | Et | Cl | H | 3-Et | 4-OH | H | 171-172.5 | 307 (M+), 134 (100%) | 4A |
| 133 | i-Pr | Cl | H | 3-O-n-Pr | 4-OH | H | 137-138 | 351 (M+), 145 (100%) | 4A |
| 134 | Et | Cl | H | 3-O-n-Pr | 4-OH | H | 95-95.5 | 337 (M+), 122 (100%) | 4A |
| 135 | i-Pr | Cl | H | 3-OEt | 4-OH | H | 183-184.5 | 337 (M+), 145 (100%) | 4A |
| 136 | Et | Cl | H | 3-OEt | 4-OH | H | 153.5-154.5 | 323 (M+), 145 (100%) | 4A |
| 137 | i-Pr | Cl | H | 3-OH | H | H | 194.5-196 | see Example 4A | 4A |
| 138 | i-Pr | Cl | H | 3-OH | 4-OMe | H | 175.5-176 | 323 (M+), 137 (100%) | 4A |
| 139 | i-Pr | Cl | H | 3-O—$(CH_2)_4CO_2$t-$B_u$ | H | H | Viscous oily susbstance | see Example 5A | 5A |
| 140 | i-Pr | Cl | H | 4-CHO | H | H | 93.5-95 | see Example 14A | 14A |
| 141 | i-Pr | Cl | H | 3-O—$(CH_2)_4CO_2$t-$B_u$ | 4-OMe | H | Viscous oily substance | 479 (M+), 237 (100%) | 5A |
| 142 | i-Pr | Cl | H | 3-O—$(CH_2)_4CO_2H$ | H | H | Viscous oily substance | see Example 6A | 6A |
| 143 | i-Pr | Cl | H | 3-O—$(CH_2)_4CO_2H$ | 4-OMe | H | Viscous oily substance | 423 (M+), 145 (100%) | 6A |
| 144 | i-Pr | Cl | H | 3-O—$(CH_2)_4CO_2Me$ | H | H | Viscous oily substance | see Example 7A | 7A |
| 145 | i-Pr | Cl | H | 3-O—$(CH_2)_4CO_2Me$ | 4-OMe | H | 94-95 | 437 (M+) | 7A |
| 146 | i-Pr | Cl | H | 3-O—$(CH_2)_4CONHMe$ | H | H | Viscous oily substance | see Example 8A | 8A |
| 147 | i-Pr | Cl | H | 3-O—$(CH_2)_5OH$ | H | H | Viscous oily substance | see Example 9A | 9A |
| 148 | i-Pr | Cl | H | 3-O—$(CH_2)_2OMe$ | 4-OMe | H | Simi-solid substance | 381 (M+), 195 (100%) | 5A |
| 149 | i-Pr | Cl | Me | 3-O—$(CH_2)_5OMe$ | H | H | Viscous oily substance | see Example 10A | 10A |
| 150 | i-Pr | Cl | Me | 3-O—$(CH_2)_5OH$ | H | H | Viscous oily substance | see Example 11A | 11A |
| 151 | i-Pr | Me | H | 4-OMe | H | H | 172-174 | see Example 12A | 12A |
| 152 | i-Pr | Me | H | 3-OEt | H | H | 167-170 | 301 (M+), 244 (100%) | 12A |
| 153 | i-Pr | Me | H | 3-O-n-Pr | 4-OMe | H | 127-128 | 345 (M+), 179 (100%) | 12A |
| 154 | Et | Br | H | 4-OMe | H | H | 96 | 337 (M+), 121 (100%) | 15A |
| 155 | Et | Br | H | 4-OEt | H | H | 87 | 351 (M+), 135 (100%) | 15A |
| 156 | Et | Br | H | 3-OEt | H | H | 108 | 351 (M+), 272 (100%) | 15A |
| 157 | Et | Br | H | 3-O-n-Pr | H | H | 88 | 365 (M+), 286 (100%) | 15A |
| 158 | Et | Br | H | 2-Me | 4-Me | H | 131-134 | 335 (M+), 119 (100%) | 15A |
| 159 | Et | Br | H | 2-OMe | 4-OMe | H | 98 | 367 (M+), 151 (100%) | 15A |
| 160 | Et | Br | H | 3-OEt | 4-OMe | H | 105 | 381 (M+), 165 (100%) | 15A |
| 161 | Et | Br | H | 3-O-n-Pr | 4-OMe | H | 78 | 395 (M+), 179 (100%) | 15A |
| 162 | i-Pr | Br | H | 4-OMe | H | H | 131.5 | 351 (M+), 121 (100%) | 15A |
| 163 | i-Pr | Br | H | 3-OMe | H | H | 127.5 | 351 (M+), 272 (100%) | 15A |
| 164 | i-Pr | Br | H | 4-OEt | H | H | 151-152.5 | see Example 15A | 15A |
| 165 | i-Pr | Br | H | 3-OEt | H | H | 136-137.5 | 365 (M+), 284 (100%) | 15A |
| 166 | i-Pr | Br | H | 3-OEt | 4-OMe | H | 115-117 | 395 (M+), 165 (100%) | 15A |
| 167 | i-Pr | Br | H | 3-O-n-Pr | 4-OMe | H | 94-97 | 409 (M+), 179 (100%) | 15A |
| 168 | i-Pr | Br | H | 2-Me | 4-Me | H | 171-173 | 349 (M+), 119 (100%) | 15A |
| 169 | i-Pr | Br | H | 2-OMe | 4-OMe | H | 117 | 381 (M+), 151 (100%) | 15A |

Now, Formulation Examples of the compounds of the formula I will be given.

FORMULATION EXAMPLE 1 (Tablets)

| | |
|---|---|
| Compound No. 44 | 10 g |
| Lactose | 20 g |
| Starch | 4 g |
| Starch for paste | 1 g |
| Magnesium stearate | 100 mg |
| Carboxymethyl cellulose calcium | 7 g |

FORMULATION EXAMPLE 1 (Tablets) -continued

| | |
|---|---|
| Total | 42.1 g |

The above components were mixed in a usual manner, and formulated into sugar-coated tablets each containing 50 mg of an active ingredient.

FORMULATION EXAMPLE 2 (Capsules)

| | |
|---|---|
| Compound No. 15 | 10 g |
| Lactose | 20 g |
| Crystal cellulose powder | 10 g |
| Magnesium stearate | 1 g |
| Total | 41 g |

The above components were mixed in a usual manner, and filled into a gelatin capsule to obtain capsules each containing 50 mg of an active ingredient.

FORMULATION EXAMPLE 3 (Soft capsules)

| | |
|---|---|
| Compound No. 15 | 10 g |
| Corn oil | 35 g |
| Total | 45 g |

The above components were mixed in a usual manner to obtain soft capsules.

FORMULATION EXAMPLE 4 (Ointment)

| | |
|---|---|
| Compound No. 15 | 1.0 g |
| Olive oil | 20 g |
| White vaseline | 79 g |
| Total | 100 g |

The above components were mixed in a usual manner to obtain 1% ointment.

FORMULATION EXAMPLE 5 (Aerosol suspension)

| | |
|---|---|
| (A) | |
| Compound No. 15 | 0.25 (%) |
| Isopropyl myristate | 0.10 |
| Ethanol | 26.40 |
| (B) | |
| A 60–40% mixture of 1,2-dichlorotetrafluoroethane and 1-chloropentafluoroethane | 73.25 |

The above composition (A) was mixed. The solution mixture thereby obtained was charged in a container equipped with a valve, and the propellant (B) was injected from a valve nozzle to a gauge pressure of from about 2.46 to 2.81 kg/cm² to obtain an aerosol suspension.

FORMULATION EXAMPLE 6 (Tablets)

| | |
|---|---|
| Compound No. 89 | 10 g |
| Lactose | 20 g |
| Starch | 4 g |
| Starch for paste | 1 g |
| Magnesium stearate | 100 mg |
| Carboxymethyl cellulose calcium | 7 g |
| Total | 42.1 g |

The above components were mixed in a usual manner, and formulated into sugar-coated tablets each containing 50 mg of an active ingredient.

FORMULATION EXAMPLE 7 (Capsules)

| | |
|---|---|
| Compound No. 87 | 10 g |
| Lactose | 20 g |
| Crystal cellulose powder | 10 g |
| Magnesium stearate | 1 g |
| Total | 41 g |

The above components were mixed in a usual manner, and filled into a gelatin capsule to obtain a capsules each containing 50 mg of an active ingredient.

FORMULATION EXAMPLE 8 (Soft capsules)

| | |
|---|---|
| Compound No. 80 | 10 g |
| Corn oil | 35 g |
| Total | 45 g |

The above components were mixed in a usual manner to obtain soft capsules.

FORMULATION EXAMPLE 9 (Ointment)

| | |
|---|---|
| Compound No. 97 | 1.0 g |
| Olive oil | 20 g |
| White vaseline | 79 g |
| Total | 100 g |

The above components were mixed in a usual manner to obtain 1% ointment.

FORMULATION EXAMPLE 10 (Aerosol suspension)

| | |
|---|---|
| (A) | |
| Compound No. 105 | 0.25 (%) |
| Isopropyl myristate | 0.10 |
| Ethanol | 26.40 |
| (B) | |
| A 60–40% mixture of 1,2-dichlorotetrafluoroethane and 1-chloropentafluoroethane | 73.25 |

An aerosol suspension was prepared from the above composition (A) and the propellant (B) in accordance with Formulation Example 5.

We claim:

1. A 3(2H)pyridazinone of the formula:

[Chemical structure: pyridazinone ring with $R_1-N$, $R_2$, and $-N(R_3)-CH_2-$ linked to a phenyl ring bearing $Y_1$, $Y_2$, $Y_3$ substituents]

wherein
$R_1$ is $C_2-C_5$ alkyl;
$R_2$ is hydrogen, $C_1-C_3$ alkyl, chlorine or bromine;
$R_3$ is hydrogen or $C_1-C_4$ alkyl; and
each of $Y_1$ and $Y_2$ which may be the same or different, is (a) hydrogen; (b) $C_1-C_8$ alkyl; (c) $C_2-C_8$ alkenyl; (d) halogen; (e) $-(CH_2)_l A$, wherein A is substituted amino of the formula $-NR_4R_5$ (wherein each of $R_4$ and $R_5$ which may be the same or different is $C_1$-$C_4$ alkyl, or $R_4$ and $R_5$ together form $C_4$-$C_6$ alkylene), morpholino, 4-$R_6$-piperazin-1-yl (wherein $R_6$ is $C_1$-$C_3$ alkyl) or —$OR_7$ (wherein $R_7$ is hydrogen or $C_1$-$C_4$ alkyl), and l is an integer of 0 to 3; (f) —$OR_8$, wherein $R_8$ is $C_4$-$C_8$ alkyl; $C_3$-$C_5$ alkenyl, benzyl or —$(CH_2)_q$-$R_9$ (wherein $R_9$ is $CO_2R_3$, —$CONHR_3$ or —$CH_2OR_7$ and q is an integer of 1 to 5); (g) —$CO_2R_3$; (h) —$CONR_{10}R_{11}$, which may be the same or different, is hydrogen, $C_{1-4}$ alkyl or $C_3$-$C_5$ alkenyl, or $R_{10}$ and $R_{11}$ together form $C_4$-$C_6$ alkylene, —$(CH_2)_2O(CH_2)_2$— or —$(CH_2)_2NR_6(CH_2)_2$—; (i) —$CONH(CH_2)_mA$, wherein A is as defined above, and m is an integer of 2 to 4; (j) —$CH=CHCOR_{12}$, wherein $R_{12}$ is hydrogen, $C_1$-$C_4$ alkoxy or —$NR_{13}(CH_2)_nCO_2R_3$, wherein $R_{13}$ is hydrogen, $C_1$-$C_6$ alkyl or cycloalkyl, and n is an integer of 1 to 4; (k) —$SR_{14}$, wherein $R_{14}$ is $C_1$-$C_4$ alkyl; (l) —CN or (m)

and $Y_3$ l is (c) $C_2$-$C_8$ alkenyl (d) halogen; (e) $(CH_2)_lA$ wherein A is substituted amino of the formula —$NR_4R_5$ (wherein each of $R_4$ and $R_5$ which may be the same or different is $C_1$-$C_4$ alkyl, or $R_4$ and $R_5$ together form $C_4$-$C_6$ alkylene), morpholino, 4-$R_6$-piperazin-1-yl (wherein $R_6$ is $C_1$-$C_4$ alkyl) or —$OR_7$ (wherein $R_7$ is hydrogen or $C_1$-$C_3$ alkyl), and l is an integer of 0 to 3; (f) —$OR_8$, wherein $R_8$ is $C_4$-$C_8$ alkyl, $C_3$-$C_5$ alkenyl benzyl or —$(CH_2)_q$—$R_9$ (wherein $R_9$ is $CO_2R_3$, $CONHR_3$ or —$CH_2OR_7$ and q is an integer of 1 to 5); (g) —$CO_2R_3$; (h) —$CONR_{10}R_{11}$, wherein each of $R_{10}$ and $R_{11}$ which may be the same or different, is hydrogen, $C_1$-$C_4$ alkyl or $C_3$-$C_5$ alkenyl, or $R_{10}$ and $R_{11}$ together form $C_4$-$C_6$ alkylene, —$C(H_2)_2O(CH_2)_2$—or —$(CH_2)_2NR_6(CH_2)_2$—; (i) —$CONH(CH_2)_mA$, wherein A is as defined above, and m is an integer of 2 to 4; (j) —$CH=CHCOR_{12}$, wherein $R_{12}$ is a hydroxy, $C_1$-$C_4$ alkoxy or —$NR_{13}(CH_2)_nCO_2R_3$, wherein $R_{13}$ is hydrogen, $C_1$-$C_6$ alkyl or cycloalkyl, and n is an integer of 1 to 4; (k) —$SR_{14}$, wherein $R_{14}$ is $C_1$-$C_4$ alkyl; (l) —CN or (m)

or, two or $Y_1$, $Y_2$ and $Y_3$ together form —$O(CH_2)_pO$—wherein p is an integer of 1 to 2; or a pharmaceutically acceptable salt thereof.

2. The pyridazinone according to claim 1, wherein $R_1$ is $C_2$-$C_4$ alkyl, $R_2$ is methyl, chlorine or bromine, $R_3$ is hydrogen, and each of $Y_1$ and $Y_2$ which may be the same or different, is hydrogen, $C_1$-$C_3$ alkyl, $C_1$-$C_5$ alkoxy or hydroxy, and $Y_3$ is $C_1$-$C_5$ alkoxy or hydroxy, or two or $Y_1$, $Y_2$ and $Y_3$ together form methylenedioxy.

3. The pyridazinone according to claim 1, wherein $R_1$ is ethyl or i-propyl, $R_2$ is methyl, chlorine or bromine, $R_3$ is hydrogen, $Y_1$ is hydrogen, and $Y_2$ is hydrogen, methyl, ethyl, methoxy, ethoxy, n-propoxy, and $Y_3$ is methoxy, ethoxy, or n-propoxyl, or $Y_2$ and $Y_3$ together form methylenedioxy.

4. The pyridazinone according to claim 1, which is 4-chloro-5-(3-ethyl-4-methoxybenzylamino)-2-ethyl-3(2H)-pyridazinone,
4-chloro-5-(3-ethoxybenzylamino)-2-ethyl-3(2H)-pyridazinone,
4-chloro-5-(3-n-propoxybenzylamino)-2-ethyl-3(2H)-pyridazinone,
4-chloro-5-(3-n-propoxy-4-methoxybenzylamino)-2-ethyl-3(2H)-pyridazinone,
4-chloro-5-(3-ethoxybenzylamino)-2-i-propyl-3(2H)pyridazinone,
4-chloro-5-(4-ethoxybenzylamino)-2-i-proyl-3(2H)-pyridazinone,
4-chloro-5-(2,4-dimethoxybenzylamino)-2-i-propyl-3(2H)-pyridazinone,
4-chloro-5-(3,4-methylenedioxybenzylamino)-2-i-propyl-3(2)pyridazinone,
4-chloro-5-(3-ethoxy-4-methoxybenzylamino)-2-i-propyl-3(2)pyridazinone,
4-chloro-5-(3-n-propoxy-4-methoxybenzylamino)-2-i-propyl-3(2H)pyridazinone,
4-bromo-5-(4-methoxybenzylamino)-2-ethyl-3(2H)-pyridazinone,
4-bromo-5-(3-n-propoxy-4-methoxybenzylamino)-2-ethyl-3(2H)pyridazinone,
4-chloro-5-(3,4-dimethoxybenzylamino)-2-i-propyl-3(2H)pyridazinone,
4methyl-5-(4-methoxybenzylamino)-2-i-propyl-3(2H)pyridazinone,
4-methyl-5-(3-ethoxybenzylamino)-2-i-propyl-3(2H)pyridazinone,
4-chloro-5-(3-ethyl-4-methoxybenzylamino)-2-i-propyl-3(2H)pyridazinone,
4-bromo-5-(3-n-propoxy-4-methoxybenzylamino)-2-i-propyl-3(2H)pyridazinone,
4-chloro-5-(2,4-dimethoxybenzylamino)-2-ethyl-3(2H)-pyridazinone,
4-bromo-5-(2,4-dimethoxybenzylamino)-2-i-proyl-3(2H)-pyridazinone,
4-chloro-5-(3-hydroxybenzylamino)-2-i-propyl-3(2H)-pyridazinone,
4-chloro-5-(2-ethoxybenzylamino)-2-i-propyl-3(2H)-pyridazinone, or
4-bromo-5-(4-methoxybenzylamino)-2-i-propyl-3(2H)-pyridazinone.

5. An anti-allergic agent comprising an anti-allergically effective amount of a 3(2) pyridazinone as defined in claim 1 or a pharmaceutically acceptable salt thereof, and a pharmaceutically acceptable carrier.

6. The pyridazinone according to claim 1, wherein $R_2$ is $C_1$-$C_3$ alkyl, chlorine or bromine, and
each of $Y_1$ and $Y_2$ which may be the same or different, is hydrogen; $C_1$-$C_5$ alkyl; halogen; —$CO_2R_3$; —$CONR_{10}R_{11}$, wherein each of $R_{10}$ and $R_{11}$ which may be the same or different, is hydrogen, $C_1$-$C_4$ alkyl or $C_3$-$C_5$ alkenyl, or $R_{10}$ and $R_{11}$ together form —$(CH_2)_2O(CH_2)_2$—or

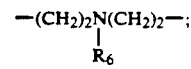

—$OR_8$, wherein $R_8$ is hydrogen, $C_1$-$C_8$ alkyl, —$(CH_2)_q$—$R_9$ (wherein $R_9$ is —$CO_2R_3$, —$CONHR_3$ or —$CH_2OR_7$); —$NR_4R_5$; morpholino; 4—$R_6$-piperazin-1-yl; —$SR_{14}$; —CN or —CHO; and $Y_3$ is halogen; —$CO_2R_3$; —$CONR_{10}R_{11}$, wherein each of $R_{10}$ and $R_{11}$ which may be the same or different, is hydrogen, $C_1$-$C_4$ alkyl or $C_3$-$C_5$ alkenyl, or $R_{10}$ and $R_{11}$ together form —$(CH_2)_2O(CH_2)_2$— or

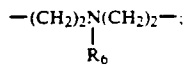

—$OR_8$, wherein $R_8$ is hydrogen, $C_1$-$C_8$ alkyl, —$(CH_2)_q$-$R_9$ wherein $R_9$ is —$CO_2R_3$, —$CONHR_3$ or —$CH_2OR_7$); —$NR_4R_5$; morpholino; 4-$R_6$-piperazin-1-yl; —$SR_{14}$; —CN or —CHO; or two of $Y_1$, $Y_2$ and $Y_3$ together form methylenedioxy.

7. The pyridazinone according to claim 1, wherein $R_1$ is $C_2$-$C_4$ alkyl;
$R_2$ is $C_1$-$C_2$ alkyl, chlorine or bromine; and
each of $Y_1$ and $Y_2$ which may be the same or different, is hydrogen; $C_1$-$C_5$ alkyl; halogen; —$CO_2R_3$; —$CONR_{10}R_{11}$, wherein each of $R_{10}$ and $R_{11}$ which may be the same or different, is hydrogen or $C_1$-$C_4$ alkyl; —$OR_8$, wherein $R_8$ is hydrogen or $C_1$-$C_5$ alkyl; dimethylamino; methylmercaptio; —CN or —CHO; and $Y_3$ is halogen; —$CO_2R_3$; —$CONR_{10}R_{11}$, wherein each of $R_{10}$ and $R_{11}$ which may be the same or different, is hydrogen or $C_1$-$C_4$ alkyl; —$OR_8$, wherein $R_8$ is hydrogen or $C_1$-$C_5$ alkyl; dimethylamino; methylmercaptio; —CN or —CHO; or two of $Y_1$, $Y_2$ and $Y_3$ together form methylenedioxy.

8. The pyridazinone according to claim 1, wherein said pyridazinone is 4-bromo-5-(3-n-propoxy-4-methoxybenzylamino)-2-ethyl-3(2H)-pyridazinone.

9. A method of reducing the incidence or severity of allergy induced in a subject by SRS-A, which comprises administering to said subject an amount effective to reduce the incidence or severity of the allergy of a 3(2H)pyridazinone as defined in claim 1 or a pharmaceutically acceptable salt thereof.

10. The pyridazinone according to claim 1, wherein said pyridazinone is 4-chloro-5(3-n-propoxy-4-methoxybenzylamino)-2-ethyl-3(2H)-pyridazinone.

11. The pyridazinone according to claim 1, wherein said pyridazinone is 4-chloro-5-(2,4-dimethoxybenzylamino)-2-isopropyl-3(2H)-pyridazinone.

* * * * *

UNITED STATES PATENT AND TRADEMARK OFFICE
CERTIFICATE OF CORRECTION

PATENT NO.   :   5,098,900

DATED        :   Mar. 24, 1992

INVENTOR(S)  :   Motoo Mutsukado, et al.

Page 1 of 2

It is certified that error appears in the above-identified patent and that said Letters Patent is hereby corrected as shown below:

Columns 9 and 10, should be deleted and substitute therefor columns 9 and 10, as shown on the attached page.

Signed and Sealed this

Eighteenth Day of August, 1992

*Attest:*

DOUGLAS B. COMER

*Attesting Officer*

*Acting Commissioner of Patents and Trademarks* acetic acid, trifluoroacetic acid or Lewis acid. A proper method for reduction is selected taking into account the substituents $Y_1$, $Y_2$ and $Y_3$ on the phenyl ring, the economy and the chemical stability. For instance, the reduction method (1) is suitable when the substituents $Y_1$, $Y_2$ and $Y_3$ have a substituent such as alkyl or alkoxy which is durable against a relatively strong reducing agent. Whereas, the reduction method (2) which is a relatively mild reduction method, is suitable when the substituents have a relatively unstable substituent such as a halogen, an olefin, an ester, an amine or an amide.

Process E is directed to the preparation of a benzylamine derivative having an amide bond by reacting a benzylamine having $CO_2H$ as a substituent with a corresponding amine in the pressure of a dehydrating condensation agent such as N,N'-carbonyldiimidazole, N,N'-dicyclohexylcarbodiimide or ethyl chlorocarbonate.

Process F is directed to the preparation of a benzylamine having a substituted aminoalkyl group on the phenyl ring by treating a benzylamine derivative obtained by e.g. Process E with a reducing agent such as lithium aluminum hydride.

In general, a benzylamine reacts with carbon dioxide in air to form a carbonate. Therefore, for its isolation, it is advantageous, in most cases, to obtain it in the form of an acid salt such as a hydrochlorate or a sulfate. A hydrochlorate of benzylamine may be subjected by itself to the reaction with 4,5-di-(chloro or bromo-)-3(2H)pyridazinone.

The compound of the formula I wherein one, two or three of the substituents $Y_1$, $Y_2$ and $Y_3$ are $-C_2R_{15}$ (wherein $R_{15}$ is $C_1-C_4$ alkyl), may readily be prepared by esterifying a compound having the corresponding carboxyl group or its salt with a dialkyl sulfuric acid ester of the formula $(R_{15}O)_2(SO_4$ (wherein $R_{15}$ is $C_1-C_4$alkyl) in the presence of an acid-binding agent such as sodium hydroxide, potassium hydroxide, potassium or sodium carbonate or bicarbonate, or an organic amine, as shown in reaction scheme 6.

Reaction scheme 6

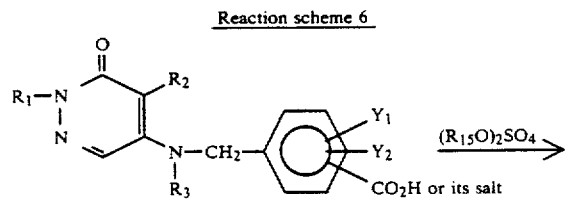

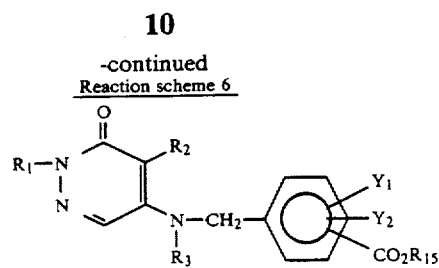

(wherein $R_1$, $R_2$, $R_3$, $Y_1$, $Y_2$ and $R_{15}$ are the same as defined above with respect to the formula I.)

The compound of the formula I wherein one, two or of the substituents $Y_1$, $Y_2$ and $Y_3$ are $-CON(R)(R_{11})$, may readily be prepared by dehydrating and condensing a compound having the corresponding carboxyl group or its salt with $HN(R_{10})(R_{11})$ in the presence of a dehydrating condensation agent such as N,N'-carbonyldiimidazole, N,N'-dicyclohexylcarbodiimide or ethyl chlorocarbonate, as shown in reaction scheme 7.

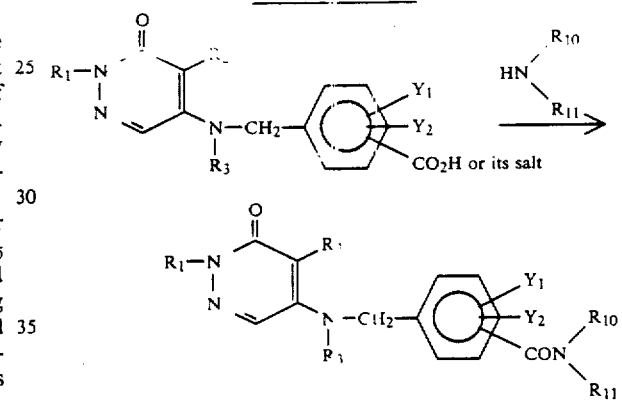

(wherein $R_1$, $R_2$, $R_3$, $R_{10}$, $R_{11}$, $Y_1$ and $Y_2$ are the same as defined above with respect to the formula I.)

The compound of the formula I wherein one, two or three of the substituents $Y_1$, $Y_2$ and $Y_3$ are hydroxyl groups, may be prepared by directly reacting the corresponding benzylamine with the 3(2H)pyridazinone of the formula II. However, it may also readily be prepared by debenzylating a compound of the formula VII having the corresponding benzyloxy group by means of catalytic hydrogenation procedure generally used, hard acid (e.g. hydrogen chloride, trifluoroacetic acid) treatment, or a combination of a soft base with a hard acid (e.g. a combination of dimethyl sulfide with boron trifluoride), as shown in reaction scheme 8.

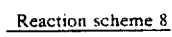
Reaction scheme 8

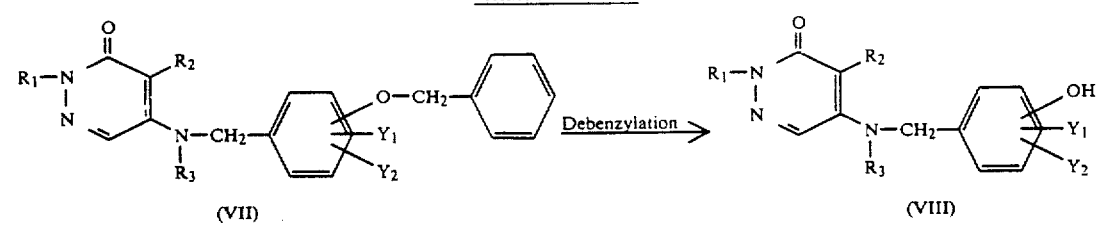

(wherein $R_1$, $R_2$, $R_3$, $Y_1$ and $Y_2$ are the same as defined above with respect to the formula I.)